United States Patent [19]

Wachter

[11] 4,256,644

[45] Mar. 17, 1981

[54] CHEMICAL INTERMEDIATES IN THE PREPARATION OF OXEPANE COMPOUNDS

[75] Inventor: Michael P. Wachter, Bloomsbury, N.J.

[73] Assignee: Ortho Pharmaceutical Corporation, Raritan, N.J.

[21] Appl. No.: 53,626

[22] Filed: Jun. 29, 1979

Related U.S. Application Data

[62] Division of Ser. No. 970,726, Dec. 18, 1978, Pat. No. 4,188,328.

[51] Int. Cl.³ .............................................. C07D 317/00
[52] U.S. Cl. .............................................. 260/340.9 R
[58] Field of Search ...................... 260/340.9 R, 333

[56] References Cited

U.S. PATENT DOCUMENTS

| | | | |
|---|---|---|---|
| 4,102,895 | 7/1978 | Kanojici et al. | 260/340.6 |
| 4,112,078 | 9/1978 | Chen | 260/333 |
| 4,112,079 | 9/1978 | Chen | 260/333 |
| 4,127,651 | 11/1978 | Chen et al. | 260/333 |
| 4,177,194 | 12/1979 | Chen | 260/333 |

FOREIGN PATENT DOCUMENTS 46-7696  2/1971  Japan .............................. 260/340.9 R

*Primary Examiner*—Ethel G. Love
*Attorney, Agent, or Firm*—Benjamin F. Lambert

[57] ABSTRACT

A method for synthesis of 2S*,3R*-3-benzyloxy-6,6-ethylenedioxy-2-methyl-2-(5'-hydroxy-4'-methylpentyl)-oxepane, an intermediate in the synthesis of 2S*,3R*-6-(2''-hydroxyethylidene)-2-methyl-2-(4',8'-dimethyl-5'-oxo-7'-nonenyl)-oxepan-3-ol, one of the active components of the zoapatle plant, is described. The natural product is useful as a utero-evacuant agent.

16 Claims, No Drawings

CHEMICAL INTERMEDIATES IN THE PREPARATION OF OXEPANE COMPOUNDS

This is a division, of application Ser. No. 970,726, filed Dec. 18, 1978, now U.S. Pat. No. 4,188,328.

In co-pending application Ser. No. 970,727 filed Dec. 18, 1978, a synthesis of racemic 2S*, 3R*-6E-(2''-hydroxyethylidene)-2-methyl-2-(4',8'-dimethyl-5'-oxo-7'-nonenyl)-oxepan-3-ol (I), one of the active components of the zoapatle plant (*Montanoa tomentosa*) and the isomeric 2S, 3R-6Z-(2''-hydroxyethylidene)-2-methyl-2-(4',8'-dimethyl-5'-oxo-7'-nonenyl)-oxepan-3-ol (II) is described. The compounds have the following chemical configuration:

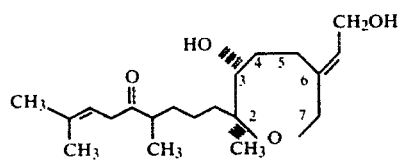

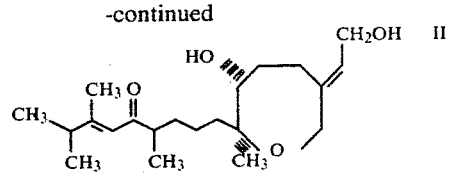

A key intermediate in the synthesis is 2S*, 3R*-3-benzyloxy-6,6-ethylenedioxy-2-methyl-2-(5'-hydroxy-4'-methylpentyl)-oxepane (III) which has the following chemical configuration:

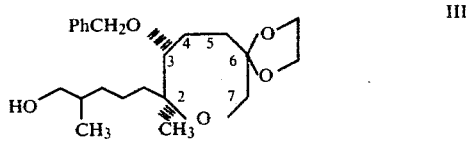

The present application relates to an alternate method of preparing the intermediate benzyloxepane compound. The synthesis is comprised of several steps which are summarized in the following schematic diagram:

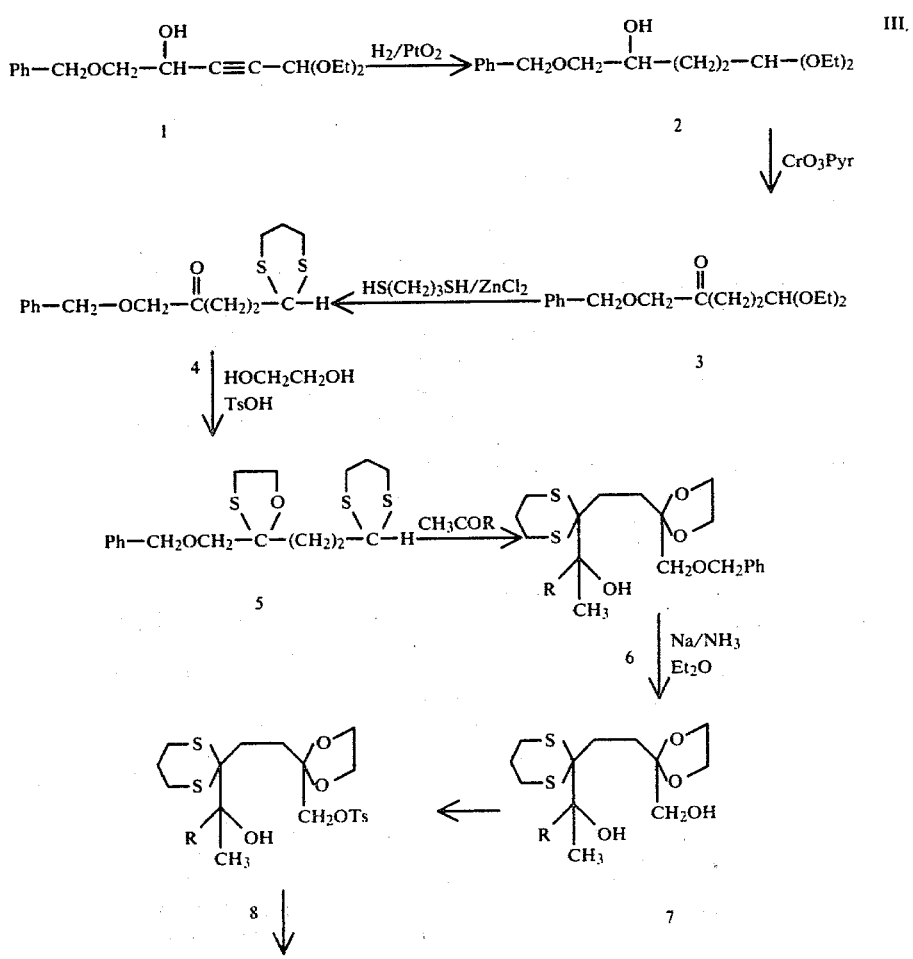

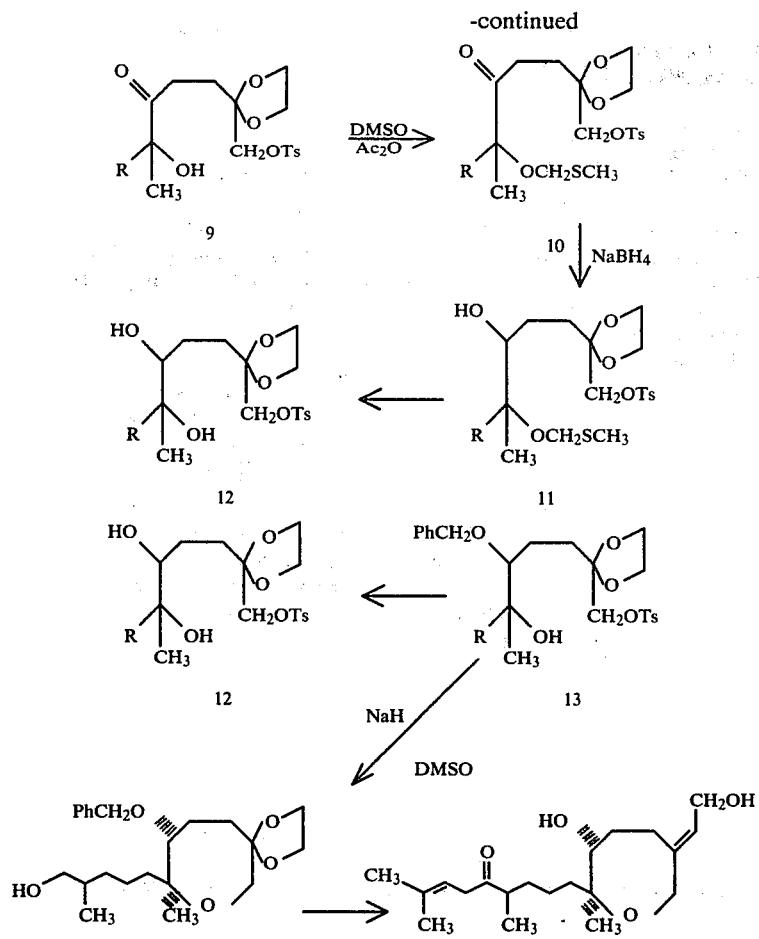

The symbols Ph, Ts and DMSO in the reaction sequence have the meaning phenyl, tosyl and dimethylsulfoxide respectively.

The first step in the synthesis of the benzyloxepane compound involves the preparation of the intermediate dithiane compound, 1-benzyloxy-2,2-ethylenedioxy-4-(1,3-dithian-2-yl)-butane (5). The dithiane compound is used to construct carbon atoms 3–7 of the oxepane ring. As shown in the diagram, the acetylenic compound (1) is first hydrogenated in a suitable solvent in the presence of a catalyst. Any catalyst capable of hydrogenating an acetylenic bond may be employed, such as, for example, platinum oxide and deactivated Raney nickel. Suitable solvents which may be employed include ethanol, methanol and tetrahydrofuran. The hydrogenation step is preferably carried out in the presence of an inorganic salt, such as sodium nitrite. The use of an inorganic salt tends to result in a cleaner product, however, the presence of a salt is not critical to the reaction. The hydrogenation product (2) is then oxidized to the corresponding ketone (3) with a suitable oxidizing agent. Oxidizing agents which can be employed include non-acidic chromium oxidizing agent such as chromium trioxide in pyridine and pyridinium chlorochromate, for example. Conversion of the diethyl acetal protecting group in compound 3 to the 1,3-dithiane protecting group in compound 4 is accomplished by reaction of the pentanone (3) with propanethiol. The reaction is preferably carried out in the presence of a Lewis acid such as, for example, zinc chloride, aluminum chloride or zinc bromide. Ketalization of the ketone with ethylene glycol under standard conditions gives the desired intermediate 1-benzyloxy-2,2-ethylenedioxy-4-(1,3-dithian-2-yl)-butane (5). The starting material, 5-benzyloxy-4-hydroxy-2-pentynal diethyl acetal (1), is prepared from acrolein diethylacetal via a four step synthesis according to the method reported in Bull. Chem. Soc. Japan, 40, 732 (1967).

The next sequence in the synthesis involves the preparation of the acyclic tertiary alcohol (6). The tertiary alcohol is prepared by condensing the lithio salt of the dithiane (5) with a methyl ketone of the formula:

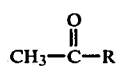

$$CH_3-\overset{O}{\underset{\|}{C}}-R \qquad IV$$

The tertiary alcohol (6) is used in constructing the side chain at the 2 position on the oxepane ring. The keto reactant, therefore, must contain a group (R) which can be converted to the side chain during the total synthesis. Such groups include a 5-t-butyldiphenylsiloxy-4-methylpentyl group, a 5-methoxyethoxymethoxy-4-methylpentyl group and a 4-methylpentenyl group. The lithio salt is prepared by treating the dithiane (5) with an alkyl lithium reagent such as, for example, butyllithium, t-butyllithium and methyllithium, in a suitable solvent such as, for example, tetrahydrofuran, pentane, hexane, ether or dioxane. The reaction is generally carried out at a temperature of about −80° C. to 20° C.; the preferred reaction temperature is between −30° C. and 0°

C. The reaction between the lithio salt and the ketone is generally carried out at a temperature between about −80° C. and 50° C. and preferably between −80° C. and 0° C. The product of the reaction (6) between the lithio salt and the dithiane (5) is isolated by standard laboratory techniques.

The methyl ketone reactants (IV) are prepared according to the methods outlined in the following diagram:

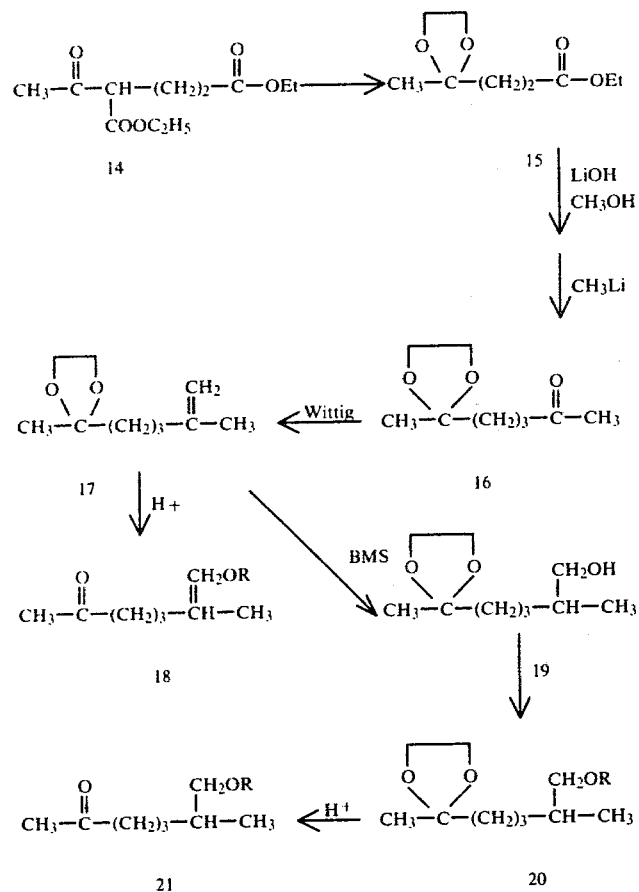

wherein R is either —Si(C₆H₅)₂-t-C₄H₉ or —CH₂OCH₂CH₂OCH₃.

The methyl ketone reactants (IV) wherein R is 5-t-butyldiphenylsiloxy-4-methylpentyl and 5-methoxyethoxymethoxy-4-methylpentyl are prepared from 6,6-ethylenedioxyheptan-2-one. A Wittig reaction carried out on the ketone (16) converts it to the corresponding ketal-olefin (17) which is then hydrolyzed with dilute acid to give the corresponding methyl ketone (18). Oxidation of the ketal-olefin (17) with borane methylsulfide gives the primary alcohol (19). Silylation of the alcohol with t-butyldiphenylsilyl chloride gives the corresponding silyl derivative (20) which is hydrolyzed to the ketone (21) with dilute acid. Similarly, treatment of the primary alcohol (19) obtained above with methoxyethoxy methyl chloride gives the corresponding methoxyethoxymethoxy protected alcohol (20) which is hydrolyzed with dilute acid to the ketone (21). The ethyl ester of 5,5-ethylenedioxy-hexanoic acid (15) is synthesized according to the method described in *Helv.*, 37, 961 (1954); *JOC*, 25, 714 (1960), and is converted to the corresponding ketone via methyllithium treatment of the lithio salt [*JOC*, 38, 3244 (1973)].

The acyclic tertiary alcohols (6) are separated from the reactants by column chromatography. The benzyl protecting group is removed with an alkali metal, i.e. sodium, lithium and potassium, in liquid ammonia to give the corresponding diols (7). Selective tosylation of the primary alcohol is achieved by treatment of the diol with tosyl chloride or mesyl chloride in a basic medium such as pyridine at room temperature. Removal of the dithiane blocking group is achieved by reaction with a deblocking agent such as, for example, mercuric chloride, N-chlorosuccinimide, silver nitrate and calcium carbonate in a suitable solvent such as, for example, acetonitrile to give the corresponding α-hydroxy ketones (9).

Treatment of the α-hydroxy ketone (9) with dimethyl sulfoxide in a solvent such as acetic anhydride or propionic anhydride gives the methylthiomethyl ether (10) which is reduced with sodium borohydride to give a mixture of hydroxy methylthiomethyl ethers (11). The erythro and threo epimers (11) can be separated by chromatography. Suitable adsorbents for the chromatography include silica and alumina. Solvents which may be employed include ethyl acetate-hexane, methylene chloride-hexane and chloroform-ethyl acetate. Removal of the protecting group on the alcohols (11) by reaction of the epimeric mixture or either the erythro or the threo isomer with a mixture of mercuric chloride and calcium carbonate in aqueous acetonitrile gives a mixture of the diols (12) or the corresponding erythro or threo isomer. Monobenzylation of the mixture of epimeric alcohols with benzyl bromide and sodium hydride in a suitable solvent such as benzene, toluene or xylene, for example, gives the epimeric benzyloxy alcohols (13). The alcohols can be separated by chromatography to give the erythro and threo epimers. Adsorbents such as silica and alumina may be employed in the chromatography. Suitable solvents include ethyl acetatehexane, methylene chloride-hexane and chloroform-ethyl acetate. Alternatively, the erythro epimer can be obtained by benzylation of the erythro diol (12) obtained above. Cyclization of the benzylated erythro alcohol (13) wherein R is a 5-t-butyldiphenylsiloxy-4-methylpentyl group with a suitable base in dimethyl sulfoxide gives the benzyloxyl oxepane intermediate (III). Suitable bases include potassium hydroxide, sodium hydroxide, lithium hydride, potassium hydride and sodium hydride. The cyclization reaction is generally carried out at a temperature between room temperature and 100° C. The preferred reaction temperature is about 50° C. to 75° C. Cyclization of the threo epimer gives the corresponding benzyloxy oxepane intermediate. When the cyclization reaction is carried out on the compound wherein the protecting group (R) is a 5-methoxyethoxymethoxy-4-methylpentyl group with sodium hydride/dimethyl sulfoxide as described above, the corresponding protected primary alcohol is obtained. Removal of the protecting group is accomplished with zinc chloride at room temperature in a suitable solvent such as methylene chloride or with tosic acid in a hydrocarbon solvent such as benzene to give the primary alcohol (III). The reaction with tosic acid is preferably carried out at the reflux temperature of the solvent.

When the cyclization is carried out on the compound wherein the protecting group (R) is a 4-methylpentenyl group as described above, the corresponding oxepane is obtained which is then oxidized with borane methylsulfide to give the primary alcohol (III).

As disclosed in Ser. No. 970,727, the benzyloxy intermediate 2S*, 3R*-3-benzyloxy-6,6-ethylenedioxy-2-methyl-2-(5'-hydroxy-4'-methylpentyl)-oxepane is converted to 2S*, 3R*-6-(2''-hydroxyethylidene)-2-methyl-2-(4',8'-dimethyl-5'-oxo-7'-nonenyl)-oxepan-3-ol by a series of reactions resulting in a racemic mixture of one of the active components in the zoapatle plant. The compound is useful as a utero-evacuant agent.

The following examples describe the invention in greater detail and are intended to be a way of illustrating and not limiting the invention.

The synthesis of the benzyloxy oxepane intermediate is illustrated by the following examples.

EXAMPLE 1

5-Benzyloxy-4-hydroxypentanal diethyl acetal

A solution of 5-benzyloxy-4-hydroxy-2-pentynal diethyl acetal (43.2 g) in abs. ethanol (250 ml) is hydrogenated in the presence of 82.7% platinum oxide (1.4 g), sodium nitrite (14 mg) and 1 drop of water for 90 minutes in a Parr hydrogenation apparatus. The reaction is repeated exactly as above with another (43.2 g) portion of 5-benzyloxy-4-hydroxy-2-pentynal diethyl acetal; the two mixtures are combined and the catalyst is removed by filtration through a bed of celite and washed with ethanol. The combined filtrate is evaporated in vacuo to give a residue (89.4 g, 100%). A 200 mg portion of the residue is purified on Quantagram PQ1F plates (developed in 40% CHCl₃/hexane three successive times).

The principal band is eluted with ethyl acetate and the solvent is evaporated in vacuo to give 5-benzyloxy-4-hydroxypentanal diethyl acetate (152 mg); ir (neat) 2.88 μ (OH); nmr (CDCl₃,δ): 1.17 (t, 6H, OCH₂CH₃), 1.62 (m, 4H, CHCH₂CH₂CH), 2.7 (b, 1H, >CH-OH), 3.53 (m, 7H, OCH₂CH₃ and OCH₂CH and

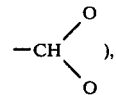

4.47 (m, 1H, >CHOH), 4.5 (s, 2H φCH₂O), 7.28 (s, 5H, φCH₂O).

EXAMPLE 2

5-Benzyloxy-1,1-diethoxy-pentan-4-one

Chromium trioxide (193 g) is added to a slurry of methylene chloride (6.9 l), dry pyridine (308 ml) and dry celite (402 g). After stirring for 45 minutes, 5-benzyloxy-4-hydroxypentanal diethyl acetal (88.9 g) in methylene chloride (950 ml) is added dropwise and the mixture is stirred overnight at room temperature. The celite and the salts are removed by filtration and washed with methylene chloride (9 l). The solvent is removed in vacuo and the filter cake is washed further with diethyl ether (9 l). The ether layer is added to the methylene chloride residue; the mixture is stirred for one hour, and filtered through a bed of celite. The filtrate is washed with 5% sodium bicarbonate (4 l), brine (3 l) and dried (sodium sulfate). After removal of most of the ether, the pyridine is removed with saturated copper sulfate (600 ml), and the ether layer is washed with brine (300 ml) and dried (sodium sulfate). The solvent is removed in vacuo to give an oil (85.2 g, 96.5%). A 200 mg portion of the residue is purified on Quantagram PQ1F plates (20% ethyl acetate/chloroform) to give 5-benzyloxy-1,1-diethoxy-pentan-4-one (200 mg); ir (neat) 5.79 μ (C=O); nmr (CDCl₃,δ): 1.17 (t, 6H, OCH₂CH₃), 1.9 (m, 2H, CH₂CH₂CH), 2.52 (t, 2H, CH₂CH₂CH), 3.48 (m, 4H, OCH₂CH₂), 4.03 (s, 2H, OCH₂CO), 4.45 (t, 1H,

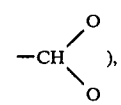

4.53 (s, 2H, φCH₂O), 7.28 (s, 5H, φCH₂O).

EXAMPLE 3

1-Benzyloxy-4-(1,3-dithian-2-yl)-butan-2-one

5-Benzyloxy-1,1-diethoxy-pentan-4-one (84.7 g) is treated in chloroform (150 ml) with 1,3-propanedithiol (33.2 g) and immediately cooled in an ice water bath. After the addition of zinc chloride (41 g) the mixture is stirred overnight at room temperature, poured into brine (1.2 l) and allowed to stir for an additional hour. The organic layer is separated, washed with 5% potassium hydroxide (1 l), brine (1.5 l) and dried (sodium sulfate). The solvent is removed in vacuo to give a yellow oil (90 g, 100%). A 250 mg portion of the oil is purified on Quantagram PQ1F plates (chloroform) to give 1-benzyloxy-4-(1,3-dithian-2-yl)-butan-2-one (230 mg); ir (neat) 5.78 μ (C=O); nmr (CDCl₃,δ): 1.97 (m, 4H, SCH₂CH₂CH₂S and CH₂CH₂CH), 2.73 (m, 6H, SCH₂CH₂CH₂S and

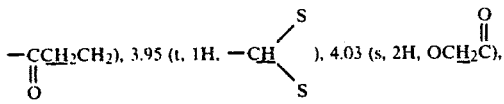

4.53 (s, 2H, φC$\underline{H}_2$O), 7.28 (s, 5H, OC$\underline{H}_2$O).

EXAMPLE 4

1-Benzyloxy-2,2-ethylenedioxy-4-(1,3-dithian-2-yl)-butane

Treatment of 1-benzyloxy-4-(1,3-dithian-2-yl)-butan-2-one (89.8 g) in benzene (3.5 l) with distilled ethylene glycol (220 ml) and p-toluenesulfonic acid (11.7 g) at reflux temperature in a Dean-Stark apparatus for 18 hours gives a mixture which is concentrated to 500 ml in vacuo and allowed to stir for one hour. After the addition of sodium carbonate (10 g), the mixture is then partitioned between ether (300 ml) and brine (300 ml). The aqueous phase is extracted with ether (600 ml) and the combined extracts are washed with 0.05% sodium carbonate (1.2 l), filtered through phase-separating paper and dried (sodium sulfate). The solvent is removed in vacuo to give a residue (102.15 g; 99%). A 200 mg portion of the residue is purified on Quantagram PQ1F plates (chloroform) to give 1-benzyloxy-2,2-ethylenedioxy-4-(1,3-dithian-2-yl)-butane (180 mg); ir (heat) C=O absent; nmr (CDCl$_3$,δ) 1.92 (m, 6H, CC$\underline{H}_2$C$\underline{H}_2$CH and

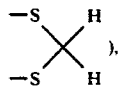

2.83 (m, 4H, SC$\underline{H}_2$CH$_2$C$\underline{H}_2$S),

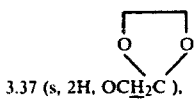

3.37 (s, 2H, OC$\underline{H}_2$C ).

3.93 (s, 5H, OC$\underline{H}_2$C$\underline{H}_2$O and —C$\underline{H}$<), 4.55 (s, 2H, φC$\underline{H}_2$O), 7.28 (s, 5H, φCH$_2$O).

EXAMPLE 5

1-Benzyloxy-11-t-butyldiphenylsiloxy-6,10-dimethyl-5,5-(1,3-propylenedithio)-2,2-ethylenedioxy-6-hydroxy-undecane 1-Benzyloxy-2,2-ethylenedioxy-4-(1,3-dithian-2-yl)-butane (19.7 g) is treated in distilled tetrahydrofuran (800 ml) with n-butyllithium (45.7 ml, 1.6 M in hexane) at −70° C. and allowed to stir below −25° C. for 2 hours. The solution is cooled to −70° C., 1-t-butyldiphenylsiloxy-2-methyl-6-oxo-heptane (25.05 g) is added and the resulting solution is stirred below 0° C. for 16 hours, concentrated to 50 ml in vacuo and partitioned between ether (500 ml) and brine (500 ml). The aqueous phase is extracted with ether (900 ml) and the combined ether extracts are washed with brine (90 ml), filtered through phase-separating paper and dried (sodium sulfate). The solvent is removed in vacuo to give a pale yellow oil (45.1 g). The oil is purified by chromatographing it twice on silica gel (ethyl acetate-hexane) to give 1-benzyloxy-11-t-butyldiphenylsiloxy-6,10-dimeth- yl-5,5-(1,3-propylenedithio-2,2-ethylenedioxy-6-hydroxy-undecane

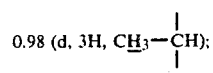

0.98 (d, 3H, C$\underline{H}_3$—CH);

1.09 [S, 9H, (C$\underline{H}_3$)$_3$—C],

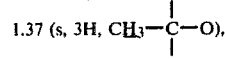

1.37 (s, 3H, C$\underline{H}_3$—C—O), 2.88 (t, 4H, —CH$_2$S—x2),

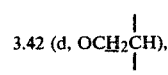

3.42 (d, OC$\underline{H}_2$CH), 4.0 (s, —OC$\underline{H}_2$C$\underline{H}_2$-O), 4.61 (s, PhC$\underline{H}_2$O—), 7.2–7.8 (m, 15H, aromatic $\underline{H}$).

EXAMPLE 6

1-Benzyloxy-6,10-dimethyl-5,5-(1,3-propylenedithio)-2,2-ethylenedioxy-6-hydroxy-11-methoxyethoxyme-thoxy-undecane 1-Benzyloxy-2,2-ethylenedioxy-4-(1,3-dithian-2-yl)-butane (0.71 g) is treated in distilled tetrahydrofuran (50 ml) with n-butyllithium (1.5 ml, 2.4 M in hexane) at 70° C., 1-methoxyethoxymethoxy-2-methyl-6-oxo-heptane (0.55 g) is added and the resulting solution is stirred below 0° C. for 16 hours, concentrated to about 2.5 ml in vacuo and partitioned between ether (50 ml) and brine (50 ml). The aqueous phase is extracted with ether (90 ml) and the combined ether extracts are washed with brine (90 ml), filtered through phase-separating paper and dried (sodium sulfate). The solvent is removed in vacuo to give a dark yellow oil (0.92 g). The oil is purified by chromatographing it twice over silica gel (chloroform-hexane) to give 1-benzyloxy-6,10-dimethyl-5,5-(1,3-propylenedithio)-2,2-ethylenedioxy-6-hydroxy-11-methoxyethoxymethoxy-undecane (0.29 g, 25%); ir (neat) 2.9 μ (OH) : nmr (CDCl$_3$,δ)

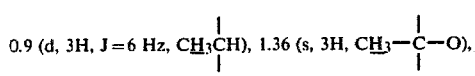

2.8 (m, 4H, C$\underline{H}_2$Sx2), 3.4 (overlapping m, 7H, OC$\underline{H}_3$,

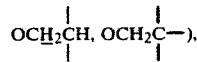

3.6 (m, 4H, dH, OC$\underline{H}_2$C$\underline{H}_2$O), 3.96 (br s, 4H, ketal O-C$\underline{H}_2$C$\underline{H}_2$O-), 4.5–4.6 (2s, 4H, OC$\underline{H}_2$O and OC$\underline{H}_2$Ph), 7.32 (s, 5H, aromatic H).

When in the above procedure 2-methyl-6-oxo-hept-1-ene is employed in place of 1-methoxyethoxyme-thoxy-2-methyl-6-oxo-heptane, 1-benzyloxy-6,10-dimethyl-5,5-(1,3-propylenedithio)-2,2-ethylenedioxy- 6-hydroxy-undec-10-ene is obtained; ir (neat) 292μ (OH); nmr (CDCl₃,γ) 0.9 (d, 3H, J=6 Hz,

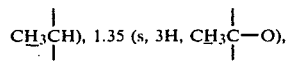

1.7 (br s, 3H, C$\underline{H}_3$—C=C),

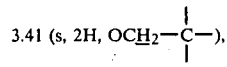

3.98 (s, 4H, OC$\underline{H}_2$CH$_2$O), 4.58 (s, 2H, OC$\underline{H}_2$Ph), 4.67 (br s, 2H, C=C$\underline{H}_2$), 7.31 (s, 5H, aromatic).

EXAMPLE 7

1,6-Dihydroxy-6,10-dimethyl-5,5-(1,3-propylenedithio)-2,2-ethylenedioxy-11-t-butyldiphenylsiloxy-undecane 1-Benzyloxy-11-t-butyldiphenylsiloxy-6,10-dimethyl-5,5-(1,3-propylenedithio)-2,2-ethylenedioxy-6-hydroxy-undecane (6.4 g) is added in ether (350 ml) to distilled liquid ammonia (350 ml). Sodium (0.85 g) is added in portions over a 15 minute period and the reaction mixture is allowed to stir vigorously for 0.2 hours. Ammonium chloride (1.8 g) is added and the ammonia is allowed to evaporate overnight. Ether and brine are added and after stirring for 45 minutes, the ether layer is removed. The aqueous phase is extracted with ether (0.5 l), and the combined ether extracts are washed with brine, filtered through phase-separating paper and dried (sodium sulfate). The solvent is removed in vacuo to give a yellow oil (5.55 g). A 150 mg portion of the oil is purified on Quantagram PQ1F plates (ethyl acetate) to give 1,6-dihydroxy-6,10-dimethyl-5,5-(1,3-propylenedithio)-2,2-ethylenedioxy-11-t-butyldiphenylsiloxy-undecane; ir (neat) 2.88 μ (OH); nmr (CDCl₃,δ), 0.91 (d, 3H, J=6Hz, C$\underline{H}_3$CH), 1.03 [s, 9H, (C$\underline{H}_3$)₃-C], 1.31 (s, 3H,CH₃—C—O), 2.83 (m, 4H, —SCH₂CH₂—S—), 3.5 [overlapping s, 4H,(C$\underline{H}_2$OH) and d (—C$\underline{H}_2$CH)], 3.99 (s, 4H, -OC$\underline{H}_2$C$\underline{H}_2$-O), 7.2–7.8 (m, aromatic $\underline{H}$).

When in the above procedure 1-benzyloxy-6,10-dimethyl-5,5-(1,3-propylenedithio)-2,2-ethylenedioxy-6-hydroxy-11-methoxyethoxymethoxy-undecane is employed in place of 1-benzyloxy-11-t-butyldiphenylsiloxy-6,10-dimethyl-5,5(1,3-propylenedithio)-2,2-ethylenedioxy-6-hydroxy-undecane, 1,6-dihydroxy-6,10-dimethyl-5-(1,3-dithian-2-yl)-2,2-ethylenedioxy-11-methoxyethoxymethoxy-undecane is obtained; ir (neat) 2.9 μ (OH).

When in the above procedure 1-benzyloxy-6,10-dimethyl-5,5-(1,3-propylenedithio)-2,2-ethylenedioxy-6-hydroxy-undec-10-ene is employed in place of 1-benzyloxy-11-t-butyldiphenylsiloxy-6,10-dimethyl-5,5-(1,3-propylene-dithio)-2,2-ethylenedioxy-6-hydroxy-undecane, 1,6-dihydroxy-6,10-dimethyl-5,5-(1,3-propylenedithio)-2,2-ethylenedioxy-undec-10-ene is obtained; ir (neat) 2.92 μ(OH), 6.1 (C=C); nmr (CDCl₃,δ)

(C=C); nmr (CDCl₃,δ) 1.35 (s, 3H, C$\underline{H}_3$—C—O), 1.7 (br s, 3H,

CH₃C=C$\underline{H}_2$), 3.5 (s, 2H, HOC$\underline{H}_2$—C—), 4.0 (s, 4H, OC$\underline{H}_2$C$\underline{H}_2$O), 4.68 (br s, 2H, $\underline{H}_2$C=C).

EXAMPLE 8

11-t-Butyldiphenylsiloxy-6,10-dimethyl-5,5-(1,3-propylenedithio)-2,2-ethylenedioxy-6-hydroxy-1-tosyloxyundecane 1,6-Dihydroxy-6,10-dimethyl-5,5-(1,3-propylenedithio)-2,2-ethylenedioxy-11-t-butyldiphenylsiloxyundecane (5.2 g) is treated in dry pyridine (35 ml) with p-toluenesulfonyl chloride (2.4 g) in pyridine (10 ml) and the mixture is allowed to stir overnight at room temperature. The reaction mixture is partitioned between ether (100 ml) and water (100 ml) and the organic phase is separated, treated with saturated copper sulfate to remove pyridine, followed by washing with brine, filtered through phase-separating paper and dried (sodium sulfate). The solvent is removed in vacuo to give 11-t-butyldiphenyl-siloxy-6,10-dimethyl-5,5-(1,3-propylenedithio)-2,2-ethylene-dioxy-6-hydroxy-1-tosyloxyundecane (6.5 g, 98%). A 200 mg) portion is further purified by chromatography on silica gel (5% ethyl acetate-hexane) nmr (CDCl₃,δ) 0.95 (d, 3H,J=6Hz, C$\underline{H}_3$CH), 1.05 [s, 9H, (C$\underline{H}_3$)₃-C],

2.43 (s, 3H, C$\underline{H}_3$Ph), 2.83 (m, 4H, (-S-C$\underline{H}_2$C$\underline{H}_2$-S-),

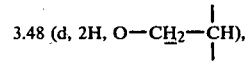

3.93 (s,4H, O-C$\underline{H}_2$C$\underline{H}_2$-O), 7.2–7.9 (m, aromatic $\underline{H}$).

When in the above procedure 1,6-dihydroxy-6,10-dimethyl-5,5-(1,3-propylenedithio)-2,2-ethylenedioxy-11-methoxyethoxymethoxyundecane is employed in place of 1,6-dihydroxy-6,10-dimethyl-5,5-(1,3-propylenedithio)-2,2-ethylenedioxy-11-t-butyldiphenyl-siloxyundecane, 6,10-dimethyl-5,5-(1,3-propylenedithio)-2,2-ethylenedioxy-6-hydroxy-11-methoxyethoxymethoxy-1-tosyloxyundecane is obtained; nmr (CDCl₃,δ)

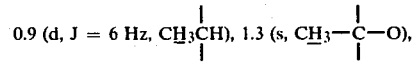

2.42 (s, 3H, C$\underline{H}_3$Ph), 2.8 (m, 4H, C$\underline{H}_2$Sx2), 3.3–3.6 (overlapping m, C$\underline{H}_3$O-,

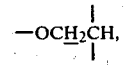

—OC$\underline{H}_2$C$\underline{H}_2$O—), 3.92 (s, 4H, ketal —OC$\underline{H}_2$C$\underline{H}_2$O—),

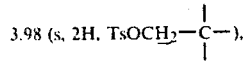

3.98 (s, 2H, TsOCH₂—C—), 4.66 (s, 2H, OCH₂ O), 7.45 (m, 4H, aromatic H).

When in the above procedure 1,6-dihydroxy-6,10-dimethyl-5,5-(1,3-propylenedithio)-2,2-ethylenedioxy-undec-10-ene is employed in place of 1,6-dihydroxy-6,10-dimethyl-5,5-(1,3-propylenedithio)-2,2-ethylenedioxy-11-t-butyldiphenylsiloxyundecane, 6,10-dimethyl-5,5-(1,3-propylenedithio)-2,2-ethylenedioxy-6-hydroxy-1-tosyloxy-undec-10-ene is obtained; nmr (CDCl₃,δ)

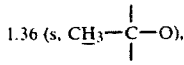

1.73 (br s, CH₃-C≡C), 2.43 (s, 3H, CH₃-Ph), 2.84 (m, 4H, —CH₂Sx2), 3.95 (br s, 6H, —OCH₂CH₂O— and

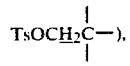

4.7 (br s, 2H, H₂C=C), 7.45 (m, 4H, aromatic H).

EXAMPLE 9

11-t-Butyldiphenylsiloxy-6,10-dimethyl-2,2-ethylenedioxy-6-hydroxy-5-oxo-1-tosyloxyundecane 11-t-Butyldiphenylsiloxy-6,10-dimethyl-5,5-(1,3-propylenedithio)-2,2-ethylenedioxy-6-hydroxy-1-tosyloxy-undecane (6.5 g) in 80% aqueous acetonitrile (500 ml) is added dropwise to a mixture of mercuric chloride (4.3 g), calcium carbonate (1.5 g) and 80% aqueous acetonitrile (500 ml) and the resulting slurry is refluxed for 18 hours. The reaction mixture is filtered through a bed of celite and washed with 1:1 methylene chloride-hexane (2 l). The organic phase is separated, washed with 5 M ammonium acetate (1 l), brine (1 l) and dried (sodium sulfate). The solvent is removed in vacuo to give a yellow oil (4.6 g). The oil is purified by chromatography on silica gel (ethyl acetate/hexane) to give 11-t-butyldiphenylsiloxy-6,10-dimethyl-2,2-ethylenedioxy-6-hydroxy-5-oxo-1-tosyloxyundecane (3.55 g, 62%); ir (neat) 2.85 μ (OH), 5.89 μ (C=O); nmr (CDCl₃, δ), 0.89 (d, CH₃CH), 1.05 [s, (CH₃)₃-C],

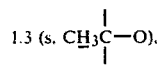

2.42 (s, 3, CH₃-Ph),

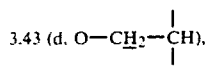

3.6 (br s, OH), 3.9 (s, OCH₂CH₂O and TsOCH₂C), 7.2-7.9 (aromatic H).

When in the above procedure 6,10-dimethyl-5,5-(1,3-propylenedithio)-2,2-ethylenedioxy-6-hydroxy-11-methoxyethoxymethoxy-1-tosyloxyundecane is employed in place of 11-t-butyldiphenylsiloxy-6,10-dimethyl-5,5-(1,3-propylenedithio)-2,2-ethylenedioxy-6-hydroxy-1-tosyloxyundecane, 6,10-dimethyl-2,2-ethylenedioxy-6-hydroxy-5-oxo-11-methoxyethoxymethoxy-1-tosyloxyundecane is obtained; ir (neat) 2.85 μ (OH), 5.87 μ (C=O), nmr (CDCl₃δ)

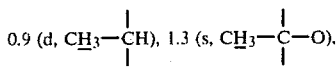

2.43 (s, CH₃ -Ph), 3.3-3.8 (overlapping m, —OCH₃,

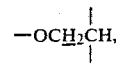

—OCH₂CH₂O—), 3.9 (s, 6H, ketal —OCH₂CH₂O—, and TsOCH₂C), 4.66 (s, 2H, —OCH₂O), 7.48 (m, 4H, aromatic H).

EXAMPLE 10

6,10-Dimethyl-2,2-ethylenedioxy-6-hydroxy-5-oxo-1tosyloxy-undec-10-ene

Silver nitrate (1.4 g) and N-chlorosuccinimide (0.99 g) are added to 80% aqueous acetonitrile (150 ml). 6,10-Dimethyl-5,5-(1,3-propylenedithio)-2,2-ethylenedioxy-6-hydroxy-1-tosyloxy-undec-10-ene (0.99 g) in 80% acetonitrile (75 ml) is added to the above solution and the mixture is stirred for 10 minutes to give a cloudy suspension. Saturated sodium thiosulfate (50 ml) is added followed by saturated sodium carbonate (50 ml) and then saturated sodium chloride solution (50 ml). A 1:1 mixture of methylene chloride:hexane (500 ml) is added and the resulting suspension is stirred for 0.5 hours and filtered through celite. The layers are separated, the aqueous layer is reextracted with methylene chloride and the combined organic extract is dried (sodium sulfate). The solvent is removed in vacuo to give an oil which is chromatographed on silica to give 6,10-dimethyl-2,2-ethylenedioxy-6-hydroxy-5-oxo-1-tosyloxy-undec-10-ene (0.258 g, 32%); nmr (CDCl₃, δ)

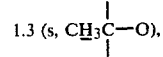

1.67 (br s, CH₃C=C), 2.43 (s, 3H, CH₃-Ph), 3.89 (s, 6H, —OCH₂CH₂O— and TsOCH₂), 4.67 (br s, 2H, H₂C=C), 7.47 (m, 4H, aromatic H).

EXAMPLE 11

11-t-Butyldiphenylsiloxy-6,10-dimethyl-2,2-ethylenedioxy-6-methylthiomethoxy-5-oxo-1-tosyloxyundecane 11-t-Butyldiphenylsiloxy-6,10-dimethyl-2,2-ethylenedioxy-6-hydroxy-5-oxo-1-tosyloxyundecane (1.15 g) is dissolved in dimethyl sulfoxide (8.15 ml), acetic anhydride (8.15 ml) is added and the resulting solution is stirred for 20 hours. The solvents are removed in vacuo below 70° C. and the residue is partitioned between ether and saturated sodium bicarbonate solution. The organic layer is washed with brine and dried (sodium sulfate). The solvent is removed in vacuo to give 11-t-butyldiphenylsiloxy-6,10-dimethyl-2,2-ethylenedioxy-6- methylthiomethoxy-5-oxo-1-tosyloxyundecane (1.13 g, 91%) as a yellow oil; nmr (CDCl$_3$,δ) 0.88 (d, C$\underline{H}$$_3$CH), 1.04 [s, (C$\underline{H}$$_3$)$_3$-C],

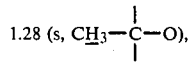
1.28 (s, C$\underline{H}$$_3$—C—O), 2.17 (s, SC$\underline{H}$$_3$), 2.42 (s, C$\underline{H}$$_3$-Ph), 3.42 (d, OC$\underline{H}$$_2$CH), 3.89 (s, OC$\underline{H}$$_2$C$\underline{H}$$_2$O and TsOC$\underline{H}$$_2$C), 4.41 (s, OC$\underline{H}$$_2$S), 7.2–7.9 (aromatic $\underline{H}$).

EXAMPLE 12

11-t-Butyldiphenylsiloxy-6,10-dimethyl-2,2-ethylenedioxy-5-hydroxy-6-methylthiomethoxy-1-tosyloxyundecane 11-t-Butyldiphenylsiloxy-6,10-dimethyl-2,2-ethylenedioxy-6-methylthiomethoxy-5-oxo-1-tosyloxyundecane (0.493 g) in methanol (30 ml) is cooled to 0° C.; sodium borohydride (0.438 g) is added and the resulting solution is stirred for 2 hours. The solvent is removed in vacuo and the residue is neutralized to pH 7 with aqueous hydrochloric acid and extracted with ether. The ether extract is washed with brine and dried over sodium sulfate. The solvent is removed in vacuo to give 11-t-butyldiphenylsiloxy-6,10-dimethyl-2,2-ethylenedioxy-5-hydroxy-6-methylthiomethoxy-1-tosyloxyundecane (0.481 g) as an epimeric mixture of alcohols. The alcohols are separated by chromatography on silica employing ethyl acetate:hexane as the eluting solvent. The epimers have the following nmr spectra:

erythro (a) CDCl$_3$,δ) 0.93 (d, C$\underline{H}$$_3$CH), 1.06 [s, (C$\underline{H}$$_3$)$_3$-C], 1.13 (s C$\underline{H}$$_3$C—O), 2.18 (s, SC$\underline{H}$$_3$), 2.43 (s, C$\underline{H}$$_3$-Ph), 3.45 (d, OC$\underline{H}$$_2$CH), 3.9 (s, —OC$\underline{H}$$_2$C$\underline{H}$$_2$O—and TsOC$\underline{H}$$_2$C), 4.51 (s, OC$\underline{H}$$_2$S), 7.2–7.9 (aromatic $\underline{H}$).

threo (b) nmr (CDCl$_3$,δ) 0.93 (d, C$\underline{H}$$_3$CH), 1.06 [s,(C$\underline{H}$$_3$)$_3$-C], 1.07 (s, C$\underline{H}$$_3$C—O), 2.18 (s, SC$\underline{H}$$_3$), 2.43 (s, C$\underline{H}$$_3$-Ph), 3.45 (d, OC$\underline{H}$$_2$CH), 3.9 (s, —OC$\underline{H}$$_2$C$\underline{H}$$_2$O— and TsOC$\underline{H}$$_2$C), 4.48 (s, OC$\underline{H}$$_2$S), 7.2–7.9 (aromatic $\underline{H}$).

EXAMPLE 13

11-t-Butyldiphenylsiloxy-5,6-dihydroxy-6,10-dimethyl-2,2-ethylenedioxy-1-tosyloxyundecane 11-t-Butyldiphenylsiloxy-6,10-dimethyl-2,2-ethylenedioxy-5-hydroxy-6-methylthiomethoxy-1-tosyloxyundecane (0.11 g) in 80% aqueous acetonitrile (5 ml) is added dropwise to a mixture of mercuric chloride (0.081 g), calcium carbonate (0.045 g) and 80% aqueous acetonitrile (2.5 ml) with the resulting slurry is stirred for 4 hours. The reaction mixture is filtered through a bed of celite and washed with diethyl ether (100 ml). The organic phase is separated, washed with 5 M ammonium acetate (30 ml), brine (25 ml) and dried (sodium sulfate). The solvent is removed in vacuo to give a yellow oil (0.084 g). The oil is further purified on Quantagram PQ1F plates (40% ethyl acetate:hexane) to give 11-t-butyldiphenylsiloxy- 5,6-dihydroxy-6,10-dimethyl-2,2-ethylenedioxy-1-tosyloxy-undecane (0.049 g) as an epidermic mixture of diols.

Treatment of erythro 11-t-butyldiphenylsiloxy-6,10-dimethyl-2,2-ethylenedioxy-5-hydroxy-6-methylthiomethoxy-1-tosyloxyundecane (0.095 g) as above gives a yellow oil (0.082 g) which is purified on Quantagram PQ1F plates (40% ethyl acetate:hexane) to give erythro 11-t-butyldiphenylsiloxy-5,6-dihydroxy-6,10-dimethyl-2,2-ethylenedioxy-1-tosyloxy-undecane (0.05 g); ir (neat) 2.85 μ (OH); nmr (CDCl$_3$,δ) 0.92 (d, C$\underline{H}$$_3$CH), 1.06 [s, (C$\underline{H}$$_3$)$_3$-C],

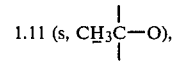
1.11 (s, C$\underline{H}$$_3$C—O), 2.43 (s, C$\underline{H}$$_3$-Ph), 3.92 (s, —OC$\underline{H}$$_2$C$\underline{H}$$_2$O— and TsOC$\underline{H}$$_2$CO), 7.2–7.9 (aromatic H).

Treatment of threo 11-t-butyldiphenylsiloxy-6,10-dimethyl-2,2-ethylenedioxy-5-hydroxy-6-methylthiomethoxy-1-tosyloxyundecane (0.11 g) as above gives a yellow oil (0.091 g) which is purified on Quantagram PQ1F plates (40% ethyl acetate:hexane) to give threo 11-t-butyl-diphenylsiloxy-5,6-dihydroxy-6,10-dimethyl-2,2-ethylene-dioxy-1-tosyloxyundecane (0.052 g); ir (neat) 2.85 μ (OH); nmr (CDCl$_3$, δ) 0.92 (d, C$\underline{H}$$_3$CH), 1.06 [s, (C$\underline{H}$$_3$)$_3$-C], 1.07

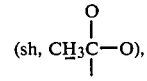
(sh, C$\underline{H}$$_3$C—O), 2.43 (s, C$\underline{H}$$_3$-Ph), 3.92 (s, —OC$\underline{H}$$_2$C$\underline{H}$$_2$O— and TsOC$\underline{H}$$_2$CO), 7.2–7.9 (aromatic H).

EXAMPLE 14

5-Benzyloxy-11-t-butyldiphenylsiloxy-6,10-dimethyl-2,2-ethylenedioxy-6-hydroxy-1-tosyloxyundecane 11-t-Butyldiphenylsiloxy-6,10-dimethyl-2,2-ethylenedioxy-5,6-dihydroxy-1-tosyloxyundecane (0.36 g) is dissolved in anhydrous benzene (1 ml) and NaH (0.026 g, 50% oil dispersion) is added at room temperature and the resulting suspension kept at room temperature for 15 minutes. Benzyl bromide (0.093 g) is added and the reaction heated at 90° C. with a strong N$_2$ sweep for 20 hours. The solvent is then evaporated, the reaction cooled and the residue treated with ice and extracted with ether and the ether dried (Na$_2$SO$_4$). A yellow oil (0.325 g) is obtained and is purified by chromatography on silica to give a mixture of benzyl ethers (0.172 g, 42%).

The mixture of benzyl ethers is further purified by chromatography on silica to give the pure erythro and threo epimers.

erythro nmr (CDCl$_3$,δ) 0.96 (d, C$\underline{H}$$_3$CH), 1.06 [s, (C$\underline{H}$$_3$)$_3$-C], 1.14 (s, C$\underline{H}_3$—C—O), 2.42 (s, C$\underline{H}_3$Ph), 3.1–3.6 (m, —OC$\underline{H}_2$CH and H$\underline{C}$—OBz), 3.9 (s, -OC$\underline{H}_2$C$\underline{H}_2$O- and TsOC$\underline{H}_2$), 4.57 (s, —OC$\underline{H}_2$-Ph), 7.2–7.9 (aromatic $\underline{H}$).

threo nmr (CDCl$_3$,δ) 0.96 (s, C$\underline{H}_3$CH), 1.06 [s, (C$\underline{H}_3$)$_3$-C and

CH$_3$—C—O], 2.41 (C$\underline{H}_3$Ph), 3.1–3.6 (m, OC$\underline{H}_2$CH and

H$\underline{C}$—OBz), 3.9 (s, —OC$\underline{H}_2$C$\underline{H}_2$O— and TsOC$\underline{H}_2$C), 4.56 (s, —OC$\underline{H}_2$Ph), 7.2–7.9 (aromatic $\underline{H}$).

Additionally, treatment of erythro 11-t-butyldiphenylsiloxy-5,6-dihydroxy-6,10-dimethyl-2,2-ethylenedioxy-1-tosyloxyundecane (0.046 g) as above gives a yellow oil (0.04 g) which is purified on Quantagram PQ1F plates (40% ethyl acetate:hexane) to give erythro 5-benzyloxy-11-t-butyldiphenylsiloxy-6,10-dimethyl-2,2-ethylenedioxy-6-hydroxy-1-tosyloxyundecane (0.012 g).

Treatment of threo 11-t-butyldiphenylsiloxy-5,6-dihydroxy-6,10-dimethyl-2,2-ethylenedioxy-1-tosyloxyundecane (0.047 g) as above gives a yellow oil (0.041 g) which is purified on Quantagram PQ1F plates (40% ethyl acetate:hexane) to give threo 5-benzyloxy-11-t-butyl-diphenylsiloxy-6,10-dimethyl-2,2-ethylenedioxy-6-hydroxy-1-tosyloxyundecane (0.011 g).

EXAMPLE 15

2S*, 3R*-3-Benzyloxy-6,6-ethylenedioxy-2-methyl-2-(5'-hydroxy-4'-methyl-pentyl)-oxepane Erythro-5-benzyloxy-11-t-butyldiphenylsiloxy-6.10-dimethyl-2,2-ethylenedioxy-6-hydroxy-1-tosyloxyundecane (0.041 g) is dissolved in DMSO (4 ml) and NaH (0.008 g, 50% oil dispersion) is added and the reaction heated to 75° C. with vigorous stirring under N$_2$. After stirring for 18 hours, the reaction mixture is cooled, poured into cold brine and hexane and stirred for 1 hour. The layers are separated and the aqueous layer is extracted 3X with hexane, the combined organic extract washed with brine and dried (Na$_2$SO$_4$). Evaporation of the solvent in vacuo gives a yellow oil which is further purified via prep tlc on silica (solvent: ethyl acetate/hexane) to give 2S*, 3R*-3-benzyloxy-6,6-ethylenedioxy-2-methyl-2-(5'-hydroxy 4'-methyl-pentyl-oxepane (0.011 g, 56%); ir (neat) 2.88 μ (OH); nmr (CDCl$_3$, δ) 0.95 (d, 3H, J=6 Hz, CH$_3$C$\underline{H}$), 1.18 (s, C$\underline{H}_3$—C—O), 3.4 (m, 5H, —OC$\underline{H}_2$—CH, —OC$\underline{H}_2$—C—, $\underline{H}$COBz), 3.92 (s, 4H, —O—C$\underline{H}_2$C$\underline{H}_2$—O—), 4.50 (ABq, 2H, J=12 Hz, —OC$\underline{H}_2$-Ph), 7.30 (s, 5H, aromatic).

EXAMPLE 16

2S*,3S*-3-Benzyloxy-6,6-ethylenedioxy-2-methyl-2-(5'-hydroxy-4'-methyl-pentyl)-oxepane Additionally, treatment of threo-5-benzyloxy-11-t-butyldiphenylsiloxy-6,10-dimethyl-2,2-ethylenedioxy-6-hydroxy-1-tosyloxyundecane (0.046 g) as above gives a yellow oil which is further purified by prep tlc (solvent: ethyl acetate/hexane) to give 2S*,3S*-3-benzyloxy-6,6-ethylenedioxy-2-methyl-2-(5'-hydroxy-4'-methylpentyl)-oxepane (0.012 g, 55%); ir (neat) 2.88 μ (OH); nmr (CDCl$_3$,δ) 0.95 (d, 3H, J=6 Hz, C$\underline{H}_3$—CH), 1.14 (s, C$\underline{H}_3$C—O), 3.2–3.7 (m, 5H, OC$\underline{H}_2$—C$\underline{H}$, OC$\underline{H}_2$—C—, $\underline{H}$C-OBz), 3.9 (br s, 4$\underline{H}$, —OC$\underline{H}_2$C$\underline{H}_2$O—), 4.47 (ABq, 2H, J=12 Hz, OC$\underline{H}_2$Ph), 7.30 (s, 5H, aromatic).

EXAMPLE 17

6,6-Ethylenedioxy-2-methyl-hept-1-ene

To a slurry of methyl triphenylphosphonium bromide (218 g) in anhydrous tetrahydrofuran (1.8 l) cooled to 0° C. is added 1.6 M n-butyllithium (270 ml) and 2.6 M n-butyl-lithium (37.5 ml). After stirring for 1 hour, 6,6-ethylene-dioxy-heptane-2-one (91.3 g) in anhydrous tetrahydrofurane (200 ml) is added dropwise and the mixture stirred for 1.5 hours at room temperature. The reaction mixture is then filtered and the filter cake washed with ether. The solvent is removed via distillation at atmospheric pressure. The crude residue is purified via vacuum distillation to give 6,6-ethylenedioxy-2-methyl-hept-1-ene (33.95 g, 38%) bp 75°@15 mm; nmr (CDCl$_3$,δ), 1.32 (s, 3H, C$\underline{H}_3$—C—), 1.7 (s, 3H, CH$_3$—C=), 3.92 (s, 4H, OC$\underline{H}_2$C$\underline{H}_2$O), 4.67 (bs, 2H, >C=C$\underline{H}_2$).

EXAMPLE 18

2-Methyl-6-oxo-hept-1-ene

A solution of 6,6-ethylenedioxy-2-methyl-hept-1-ene (12.2 g) in acetone (300 ml) and 10% hydrochloric acid (12 ml) is stirred at room temperature for 1.5 hours. The reaction is neutralized to pH 7 with a sodium bicarbonate solution and the resulting solids are filtered. The acetone is removed in vacuo and the residue is partitioned between ether and brine. The ether extract is dried (Na$_2$SO$_4$) and evaporated in vacuo to give 2-methyl-6-oxo-hept-1-ene as a pale yellow liquid (6.4 g), nmr (CDCl$_3$,δ) 1.7 (br s, C$\underline{H}_3$—C=), 2.12 (s, CH$_3$C=O), 2.4 (t, J=6 Hz, C$\underline{H}_2$C=O), 4.69 (br s, 2H, H$_2$C=C).

EXAMPLE 19

6,6-Ethylenedioxy-2-methyl-heptanol

To a solution of 6,6-ethylenedioxy-2-methyl-hept-1-ene (33.95 g) in hexane (132 ml) under a nitrogen atmosphere is added borane-methyl sulfide complex (7.05 ml) at 0° C. over a half hour period. The reaction is allowed to stir for 3 hours at room temperature and is treated with 95% ethanol (68 ml) and 3 N sodium hydroxide (21.8 ml), cooled to 0° C., followed by the dropwise addition of 30% hydrogen peroxide (24.5 ml) to maintain a temperature of 25°–35° C. The reaction mixture is heated at reflux for one half hour, poured into ice water (500 ml) and partitioned between ether and water. The aqueous phase is extracted with ether and the combined extracts are washed with brine and dried (Na$_2$SO$_4$). The solvent is removed in vacuo to give 6,6-ethylenedioxy-2-methylheptanol (33.35 g, 89%), nmr (CDCl$_3$,δ), 0.93 (d, 3H, C$\underline{H}_3$CH<),

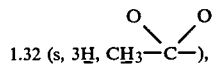

1.32 (s, 3$\underline{H}$, C$\underline{H}_3$—C—), 3.45 (bd, 2H, CHC$\underline{H}_2$O), 3.93 (s, 5H, OC$\underline{H}_2$C$\underline{H}_2$O and CH$_3$C$\underline{H}$<).

EXAMPLE 20

1-t-Butyldiphenylsiloxy-6,6-ethylenedioxy-2-methyl-heptane

Imidazole (26.5 g) is added to a solution of 6,6-ethylenedioxy-2-methyl-heptanol (33.35 g) in dimethylformamide (50 ml). A solution of t-butyldiphenylsilyl chloride (52.2 g) in dimethylformamide (200 ml) is added dropwise to the reaction mixture and allowed to stir for 3 hours at room temperature. The reaction mixture is extracted with hexane (3×300 ml) and the combined extract is washed with brine and dried (Na$_2$SO$_4$). The solvent is removed in vacuo to give 1-t-butyldiphenylsiloxy-6,6-ethylenedioxy-2-methyl-heptane (75.35 g, 99.6%); nmr (CDCl$_3$,δ), 0.91 (d, 3H, C$\underline{H}_3$CH), 1.03 [s, (C$\underline{H}_3$)$_3$C],

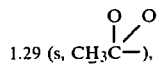

1.29 (s, C$\underline{H}_3$C—), 3.47 (d, CHC$\underline{H}_2$O), 3.88 (s, OC$\underline{H}_2$C$\underline{H}_2$O), 7.2–7.8 (m, 10 H, 2φ).

EXAMPLE 21

1-t-Butyldiphenylsiloxy-2-methyl-6-oxo-heptane 1-t-Butyldiphenylsiloxy-6,6-ethylenedioxy-2-methyl-heptane (75.35 g) in acetone (2 l) is treated with 10% hydrochloric acid (75 ml) and the solution is allowed to stir at room temperature for two and one half hours. The reaction mixture is neutralized with a saturated sodium bicarbonate solution (150 ml) the salt is removed by filtration and the solvent is removed in vacuo. The resulting residue is partitioned between ether and water, the aqueous phase is extracted with ether, and the combined ether extracts are washed with brine and dried (Na$_2$SO$_4$). The solvent is removed in vacuo to give the crude product which is purified via silica gel chromatography (5% EtOAc/hexane) to give 1-t-butyldiphenylsiloxy-2-methyl-6-oxo-heptane (61.95 g, 92%; ir (neat) 5.85μ(C=O); nmr (CDCl$_3$,δ), 0.92 (d, 3H, C$\underline{H}_3$CH<), 1.05 [s, (C$\underline{H}_3$)$_3$C], 2.07 (s, 3H, CH$_3$C=O), 3.45 (d, 2H, CHC$\underline{H}_2$), 7.2–7.8 (m, 10H, 2φ).

EXAMPLE 22

1-Methoxyethoxymethoxy-2-methyl-6-oxo-heptane 6,6-Ethylenedioxy-2-methyl-heptanol (2.0 g) is dissolved in anhydrous tetrahydrofuran (35 ml) and cooled to −78° C. under nitrogen. n-Butyllithium (0.68 g) is added and the solution is warmed to 0° C. Methoxyethoxymethyl chloride (1.59 g) is added and the reaction stirred at 0° C. for 1.5 hours. An additional 1.59 g of the chloride is added and stirring is continued at 0° C. for 2 hours. The tetrahydrofuran is evaporated in vacuo and the residue is partitioned between ether and brine. The ether extract is dried (Na$_2$SO$_4$) and the solvent is evaporated in vacuo to give 6,6-ethylenedioxy-1-methoxyethoxymethoxy-2-methylheptane. The compound is dissolved in acetone (40 ml) and 10% hydrochloric acid (2.0 ml) is added and the resulting solution is stirred for two hours. A saturated sodium bicarbonate solution (50 ml) is added, and the resulting precipitate filtered and the filtrate evaporated in vacuo. The residue is partitioned between ether and brine and the ether extract is dried (Na$_2$SO$_4$) and evporated in vacuo. The residue is chromatographed on silica (solvent: ethyl acetate/hexane) to give 1-methoxyethoxymethoxy-2-methyl-6-oxo-heptane as a colorless liquid, nmr (CDCl$_3$,δ) 0.9 (d, CH$_3$CH), 2.12 (s, CH$_3$C=O), 2.4 (t, —C$\underline{H}_2$C=O, 3.3–3.8 (m, —OC$\underline{H}_3$,

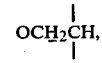

—OC$\underline{H}_2$C$\underline{H}_2$O), 4.66 (s, 2H, —OC$\underline{H}_2$O—).

Preparation of zoapatanol from (2S*, 3R*)-3-benzyloxy-6,6-ethylenedioxy-2-methyl-2-(4'-methyl-5'-hydroxypentyl)-oxepane.

EXAMPLE A

(2S*, 3R*)-3-Benzyloxy-6,6-ethylenedioxy-2-methyl-2-(4'-methyl-5'-oxopentyl)-oxepane A solution of pyridine (3.6 g, 0.0444 mol) and chromium trioxide (2.2 g, 0.0222 mol) in methylene chloride (450 ml) at 23° C. in a nitrogen atmosphere is stirred for 45 minutes. The mixture is cooled to −10° C. and celite (13 g) is added followed by (2S*, 3R*)-3-benzyloxy-6,6-ethylenedioxy-2-methyl-2-(4'-methyl-5'-hydroxypentyl)-oxepane (1.4 g, 0.0037 mol) in methylene chloride (150 ml). The mixture is stirred for 1 hour at −10° C. and 30 minutes at 0° C. The mixture is then filtered and the celite cake is washed with methylene chloride (10×50 ml). The filtrate and washings are combined and washed with saturated sodium bicarbonate (2×150 ml). The methylene chloride phase is separated, dried (MgSO$_4$) and the solvents are removed at reduced pressure. The crude product (1.3 g) is chromatographed on SilicAR CC-7 (25 g, Mallinckrodt) in hexane. Elution with 7-10% ethyl acetate/hexane gives (2S*, 3R*)-3-benzyloxy-6,6-ethylenedioxy-2-methyl-2-(4'-methyl-5'-oxopentyl)-oxepane as a clear colorless oil (1.157 g, 83%).

EXAMPLE B

(2S*, 3R*)-3-Benzyloxy-6,6-ethylenedioxy-2-methyl-2-(4',8'-dimethyl-5'-hydroxy-8'-nonenyl)-oxepane A solution of 4-bromo-2-methyl-1-butene (0.760 g, 0.0051 mol) in anhydrous tetrahydrofuran (8 ml) is added dropwise over 2 hours to a suspension of Mg turnings (126 mg, 0.0052 mol) in anhydrous tetrahydrofuran (10 ml). After stirring for 1 hour, the solution is cooled to −5° to −10° C. and a solution of (2S*, 3R*)-3-benzyloxy-6,6-ethylenedioxy-2-methyl-2-(4'-methyl-5'-oxopentyl)-oxepane (1.157 g, 0.0031 mol) is added dropwise over a period of 30 minutes. The mixture is allowed to warm to 24° C. and stirred for 30 minutes; quenched with water (5 ml), poured into saturated sodium chloride and extracted with ether (5×200 ml). The organic layers are combined, dried (MgSO$_4$) and evaporated in vacuo to give 1.4 g of a viscous light yellow oil. The oil is chromatographed on SilicAR CC-7 (30 g, Mallinckrodt) in hexane. Elution with 7-10% ethyl acetate/hexane gives (2S*, 3R*)-3-benzyloxy-6,6-ethylenedioxy-2-methyl-2-(4',8'-dimethyl-5'-hydroxy-8'-nonenyl)-oxepane as a colorless oil (1.32 g, 96%): ir (neat) 3400 cm$^{-1}$ (OH).

EXAMPLE C

(2S*, 3R*)-3-Benzyloxy-6,6-ethylenedioxy-2-methyl-2-(5'-acetoxy-4',8'-dimethyl-8'-nonenyl)-oxepane A solution of the alcohol (2S*, 3R*)-3-benzyloxy-6,6-ethylenedioxy-2-methyl-2-(4',8'-dimethyl-5'-hydroxy-8'-nonenyl)-oxepane (1.32 g, 0.0029 mol) in pyridine (10 ml) and acetic anhydride (2.7 ml) is stirred under nitrogen at 24° C. for 24 hours. The reaction mixture is poured into water and stirred for 1.5 hours. The suspension is extracted with ether (5×100 ml) and the ether extracts washed with water, saturated sodium bicarbonate, water and saturated sodium chloride, dried (MgSO$_4$) and evaporated in vacuo to give 1.5 g of a viscous, yellow oil. The oil is chromatographed on SilicAR CC-7 (30 g, Mallinckrodt) in hexane. Elution with 5-8% ethyl acetate/hexane gives (2S*, 3R*)-3-benzyloxy-6,6-ethylenedioxy-2-methyl-2-(5'-acetoxy-4',8'-dimethyl-8'-nonenyl)-oxepane (1.4 g, 97%): nmr (CDCl$_3$)δ 0.88 (d J=6, 3H, —CH—C$\underline{H}_3$), 1.18 (s, 3H, C$\underline{H}_3$), 2.02 (s, 3H, OA$\underline{c}$),

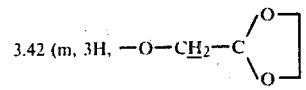

3.42 (m, 3H, —O—C$\underline{H}_2$—C⟨$^O_O$⟩)

and —C$\underline{H}$—O—CH$_2$Ph), 3.98 (s, 4H, ketal), 4.51 (d of d, J=10 Hz, 2H, O—C$\underline{H}_2$—Ph), 4.68 (broad singlet, 2H, C=C$\underline{H}_2$), 7.25 (s, 5H, aromatic).

EXAMPLE D

(2S*, 3R*)-3-Benzyloxy-6,6-ethylenedioxy-2-methyl-2-(5'-acetoxy-4', 8'-dimethyl-7'-nonenyl)-oxepane A solution of (2S*, 3R*)-3-benzyloxy-6,6-ethylenedioxy-2-methyl-2-(5'-acetoxy-4',8'-dimethyl-8'-nonenyl)-oxepane (1.4 g, 0.0028 mol) and p-toluenesulfonic acid (200 mg) in anhydrous benzene (100 ml) is refluxed for 18 hours under a nitrogen atmosphere. The mixture is cooled to room temperature, diluted with ether (350 ml) washed with saturated sodium bicarbonate, water, saturated sodium chloride, dried (MgSO$_4$) and evaporated in vacuo to give (2S*, 3R*)-3-benzyloxy-6,6-ethylenedioxy-2-methyl-2-(5'-acetoxy-4',8'-dimethyl-7'-nonenyl)-oxepane (1.4 g, 100%) as a viscous light yellow oil: ir (neat) 1714 cm$^{-1}$ (OAc): nmr (CDCl$_3$)δ 0.88 (d, J=6, 3H,—CH—C$\underline{H}_3$), 1.18 (s, 3H, CH$_3$), 2.01 (s, 3H, OA$\underline{c}$),

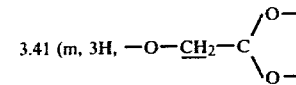

3.41 (m, 3H, —O—C$\underline{H}_2$—C⟨$^O_O$⟩)

and —C$\underline{H}$OCH$_2$Ph), 3.98 (s, 4H, ketal), 4.51 (d of d, J=10 Hz, 2H, —O—C$\underline{H}_2$Ph), 4.94 (broad m, 2H, —C$\underline{H}$—OAc and

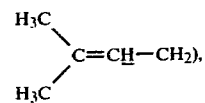

7.21 (s, 5H, aromatic).

EXAMPLE E

(2S*, 3R*)-3-Benzyloxy-6,6-ethylenedioxy-2-methyl-2-(4',8'-dimethyl-5'-hydroxy-7'-nonenyl)-oxepane A solution of (2S*, 3R*)-3-benzyloxy-6,6-ethylenedioxy-2-methyl-2-(5'-acetoxy-4',8'-dimethyl-7'-nonenyl)-oxepane (14 g, 0.00086 mol) and saturated potassium carbonate (5 ml) in methanol (30 ml) and water (10 ml) is refluxed for 4 hours. The mixture is cooled to room temperature and the methanol is evaporated under reduced pressure. The aqueous layer is extracted with ether (5×100 ml), washed in water, saturated sodium chloride, dried (MgSO$_4$), and evaporated in vacuo to give (2S*, 3R*)-3-benzyloxy-6,6-ethylenedioxy-2-methyl-2-(4',8'-dimethyl-5'-hydroxy-7'-nonenyl)-oxepane as a viscous yellow oil (1.2 g, 94%).

EXAMPLE F (2S*, 3R*)-3-Benzyloxy-6,6-ethylenedioxy-2-methyl-2-[4',8'-dimethyl-5'-(tetrahydropyran-2''-yloxy)-7'-nonenyl]-oxepane A mixture of the alcohol (2S*, 3R*)-3-benzyloxy-6,6-ethylenedioxy-2-methyl-2-(4',8'-dimethyl-5'-hydroxy-7'-nonenyl)-oxepane (1.2 g, 0.0027 mol), dihydropyran (435 mg, 0.0054 mol) and p-toluenesulfonic acid (150 mg) in anhydrous ether (15 ml) is stirred at 24° C. under a nitrogen atmosphere for 18 hours. The mixture is diluted with ether (100 ml), washed with saturated sodium bicarbonate (2×75 ml), water, saturated sodium chloride, dried (MgSO4) and evaporated in vacuo to give 1.3 g of a yellow oil. The oil is chromatographed on SilicAR CC-7 (25 g, Mallinckrodt) in hexane. Elution with 4% ethyl acetate/hexane gives (2S*, 3R*)-3-benzyloxy-6,6-ethylenedioxy-2-methyl-2-[4',8'-dimethyl-5'-(tetrahydropyran-2''-yloxy)-7'-nonenyl]-oxepane (1.20 g, 84%): nmr (CDCl3)δ 1.20 (s, 3H, CH3),

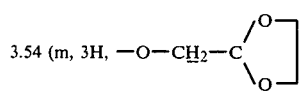

and —CH—OCH2Ph), 3.98 (s, 4H, ketal), 4.53 (d of d, J=10 Hz, 2H, —O—CH2Ph), 4.64 (broad m, 1H, —O—CH—O—),

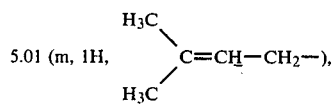

7.23 (s, 5H, aromatic).

EXAMPLE G (2S*, 3R*)-6,6-Ethylenedioxy-3-hydroxy-2-methyl-2-methyl-2-[4',8'-dimethyl-5'-(tetrahydropyran-2''-yloxy)-7'-nonenyl]-oxepane To a freshly distilled solution of ammonia (60 ml) cooled to −78° C. is added in an argon atmosphere t-butyl alcohol (1 g, 0.0135 mol). The cooling bath is removed and (2S*, 3R*)-3-benzyloxy-6,6-ethylenedioxy-2-methyl-2-[4',8'-dimethyl-5'-(tetrahydropyran-2''-yloxy)-7'-nonenyl]-oxepane (1.2 g, 0.0022 mol) in tetrahydrofuran (15 ml) is added. Freshly cut sodium metal (104 g, 0.0045 mol) is added in small pieces at −33° C. The resulting blue solution is stirred for 0.5 hours and quenched by adding ether (60 ml) followed by water (50 ml). The ammonia is evaporated at room temperature and the ether layer is separated. The water phase is extracted with ether (5×50 ml). The ether phases are combined, washed with saturated sodium chloride, dried (MgSO4) and the solvent is removed under reduced pressure. The crude product (1.0 g) is chromatographed on SilicAR CC-7 (20 g, Mallinckrodt). Elution with 10% ethyl acetate/hexane gives (2S*, 3R*)-6,6-ethylenedioxy-3-hydroxy-2-methyl-2-[4',8'-dimethyl-5'-(tetrahydropyran-2''-yloxy)-7'-nonenyl]-oxepane as a clear colorless oil (850 mg, 86%): ir (neat) 3400 cm$^{-1}$ (OH); nmr (CDCl3)δ 0.78 (d, J=6 Hz 3H, —CH—CH3), 0.82 (d, J=6 Hz, 3H, CH—CH3), 1.20 (s, 3H, CH3) 3.38

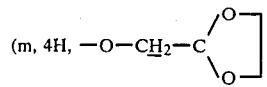

—H2C—CH—OH and —CH2—CH—OTHP), 3.98 (s, 4H, ketal), 4.56 (broad s, 1H, —O—CH—O—), 5.02 (m, 1H,

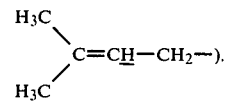

EXAMPLE H (2S*, 3R*)-3-Acetoxy-6,6-ethylenedioxy-2-methyl-2-[4',8'-dimethyl-5'-(tetrahydropyran-2''-yloxy)-7'-nonenyl]-oxepane A solution of (2S*, 3R*)-6,6-ethylenedioxy-3-hydroxy-2-methyl-2-[4',8'-dimethyl-5'-(tetrahydropyran-2''-yloxy)-7'-nonenyl]-oxepane (850 mg, 0.00193 mol) in pyridine (10 ml) and acetic anhydride (2.0 g) is stirred under nitrogen at 24° C. for 18 hours. The reaction mixture is then poured into water and stirred for 1.5 hours. The suspension is extracted with ether (5×50 ml) and the ether extracts are washed with water, and saturated sodium chloride, dried (MgSO4) and evaporated in vacuo to give (2S*, 3R*)-3-acetoxy-6,6-ethylenedioxy-2-methyl-2-[4',8'-dimethyl-5'-(tetrahydropyran-2''-yloxy)-7'-nonenyl]-oxepane (800 mg, 86%): nmr (CDCl3)δ 0.80 (d, J=6 Hz, 3H, —CH—CH3), 0.85 (d, J=6 Hz, 3H, —CH—CH3), 1.18 (s, 3H, —CH3), 2.02 (s, 3H, OAc),

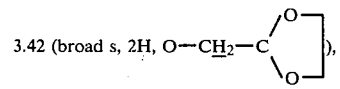

3.98 (s, 4H, ketal), 4.6 (broad s, 1H, —O—CH—O—), 5.01 (m, 2H, CH2—CH—OAc, and

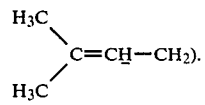

EXAMPLE I (2S*, 3R*)-3-Acetoxy-2-methyl-2-(4',8'-dimethyl-5'-hydroxy-7'-nonenyl)oxepan-6-one A mixture of (2S*, 3R*)-3-acetoxy-6,6-ethylenedioxy-2-methyl-2-[4,40 ,8'-dimethyl-5'-(tetrahydropyran-2''-yloxy)-7'-nonenyl]-oxepane (800 mg, 0.00166 mol), acetone (20 ml), water (3.5 ml) and 0.002 N sulfuric acid (11 ml) is refluxed for 24 hours under a nitrogen atmosphere. The reaction mixture is cooled to room temperature, the acetone is evaporated under reduced pressure and the aqueous layer is extracted with ether (5×50 ml). The combined organic layers are washed with saturated sodium bicarbonate, saturated sodium chloride and dried (MgSO4). The solvents are removed under reduced pressure and the crude product (520 mg)

is chromatographed on SilicAR CC-7 (10 g, Mallinckrodt) in hexane. Elution with 10–15% ethyl acetate/hexane gives (2S*, 3R*)-3-acetoxy-2-methyl-2-(4',8'-dimethyl-5'-hydroxy-7'-nonenyl)-oxypan-6-one as a colorless oil (420 mg, 71%): ir (neat) 3424 (OH), 1718 cm⁻¹ (CO and OAc): nmr (CDCl₃)δ 0.82 (d, J=6 Hz, 3H, —CH—C$\underline{H}$₃), 1.18 (s, 3H, C$\underline{H}$₃), 2.00 (s, 3H, OA$\underline{c}$), 2.5 (m, 2H, —CO—C$\underline{H}$₂—CH₂—), 3.99 (s, 2H, —O—C$\underline{H}$₂—CO—), 4.91 (m, 1H, —CH₂—C$\underline{H}$—OAc),

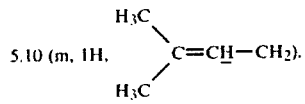

5.10 (m, 1H, ).

EXAMPLE J (2S*, 3R*)-3-Acetoxy-2-methyl-2-[4',8'-dimethyl-5'-(tetrahydropyran-2''-yloxy)-7'-nonenyl]-oxepan-6-one A mixture of (2S*, 3R*)-3-acetoxy-2-methyl-2-(4',8'-dimethyl-5'-hydroxy-7'-nonenyl)-oxepan-6-one (1.1 g), dihydropyran (500 mg) and p-toluenesulfonic acid (150 mg) in anhydrous ether (15 ml) is stirred at 24° C. under a nitrogen atmosphere for 18 hours. The mixture is then diluted with ether (100 ml), washed with saturated sodium bicarbonate (2×75 ml), water, saturated sodium chloride, dried (MgSO₄) and evaporated in vacuo to give 1.5 g of a yellow oil. The oil is chromatographed on SilicAR CC-7 (15 g) in hexane. Elution with 4% ethyl acetate/hexane gives (2S*, 3R*)-3-acetoxy-2-methyl-2-[4',8'-dimethyl-5'-(tetrahydropyran-2''-yloxy)-7'-nonenyl]-oxepan-6-one as a colorless oil (1.2 g, 88%): nmr (CDCl₃)δ 1.1 (s, 3H, —CH₃), 2.05 (s, 3H, —COCH₃), 2.62 (m, 2H, —CO—C$\underline{H}$₂—CH₂—), 4.05 (s, 2H, —O—C$\underline{H}$₂—CO—CH₂—), 4.81 (m, 1H, —O—C$\underline{H}$—CH₂—), 5.02 (m, 2H,

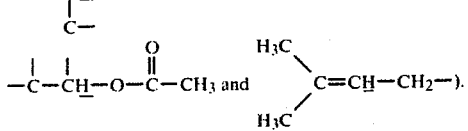

EXAMPLE K (2S*, 3R*)-3-Acetoxy-6-(2'-carboethoxymethylidene)-2-methyl-2-[4',8'-dimethyl-5'-(tetrahydropyran-2''-yloxy)-7'-nonenyl]-oxepane Triethyl phosphonoacetate (641 mg, 0.00285 mole) in benzene (9 ml) is added to a suspension of 99% sodium hydride (66 mg, 0.00279 mole) in benzene (1 ml). The mixture is heated to 70° C. and stirred for 2 hours. The mixture is then cooled to 25° C. and (2S*, 3R*)-3-acetoxy-2-methyl-2-[4',8'-dimethyl-5'-(tetrahydropyran-2''-yloxy)-7'-nonenyl]-oxepan-6-one (500 mg, 0.00114 mole) in benzene (10 ml) is added. The mixture is heated to 70° C. and stirred for 1 hour. The reaction mixture is then cooled to 0° C., diluted with ether (25 ml) and quenched with 5% dil HCl (20 ml). The organic layer is separated and the aqueous layer is extracted with ether (5×75 ml). The organic layers are combined, dried (MgSO₄) and evaporated to give 825 mg of a slightly yellow oil. The oil is chromatographed on silica gel (10 g, Baker) in hexane. Elution with 8% ethyl acetate/hexane gives (2S*, 3R*)-3-acetoxy-6-(2''-carboethoxymethylidene)-2-methyl-2-[4',8'-dimethyl-5'-(tetrahydropyran-2''-yloxy)-7'-nonenyl]-oxepane as a colorless oil (570 mg, 98%): nmr (CDCl₃)δ (0.82 (d, 3H, J=6 Hz, —CH—C$\underline{H}$₃), 1.01 (s, 3H, —C—C$\underline{H}$₃), 1.22 (t, 3H, J=6 Hz, —CH₂—C$\underline{H}$₃), 2.02 (s, 3H, —OCOC$\underline{H}$₃), 4.10 (m, 4H, J=6 Hz, —OCO—C$\underline{H}$₂CH₃ and —O—C$\underline{H}$₂—C=C$\underline{H}$—), 4.64 (m, 1H, —O—C$\underline{H}$—O—CH₂—), 5.09 (m, 2H, —C$\underline{H}$—OAc and

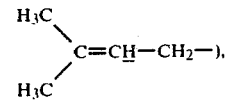

5.60 (broad s, 1H, —C=C$\underline{H}$—COOEt).

EXAMPLE L (2S*, 3R*)-6Z-(2''-Hydroxyethylidene)-2-methyl-2-[4',8'-dimethyl-5'-(tetrahydropyran-2''-yloxy)-7'-nonenyl]-oxepan-3-ol and (2S*, 3R*)-2''-Hydroxyethylidene)-2-methyl-2-[4',8'-dimethyl-5'-(tetrahydropyran-2''-yloxy)-7'-nonenyl]-oxepan-3-ol A solution of (2S*, 3R*)-3-acetoxy-6-(2''-carboethoxymethylidene)-2-methyl-2-[4',8'-dimethyl-5'-(tetrahydropyran-2''-yloxy)-7'-nonenyl]-oxepane (0.675 g, 0.00122 mole) in ether (8 ml) is added dropwise to a suspension of lithium aluminum hydride (0.205 g, 0.00532 mole) in ether (25 ml) at 0° C. under nitrogen. The mixture is stirred at 0° C. for 1 hour. The quenching of the reaction is accomplished by the addition of wet ethyl acetate (2 ml) and wet ether (8 ml). The mixture is diluted with saturated ammonium chloride solution and extracted with ether (5×50 ml). The ether phases were combined, dried (MgSO₄) and evaporated to give a slightly yellow oil (0.650 g). The material is chromatographed on silica gel (16 g, Baker) in hexane. Elution with 22% to 24% ethyl acetate/hexane gives (2S*, 3R*)-6Z-(2''-hydroxyethylidene)-2-methyl-2-[4',8'-dimethyl-5'-(tetrahydropyran-2''-yloxy)-7'-nonenyl]-oxepan-3-ol (155 mg), 0.85 (d, 3H, J=6 Hz, —CH—C$\underline{H}$₃), 1.18 (s, 3H, C$\underline{H}$₃), 2.2 (m, 4H, —CH₂—C$\underline{H}$₂—C=CH and

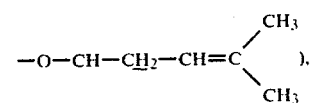

4.2 (m, 4H, —O—C$\underline{H}$₂—CH—C=CH, and C=CH—CH₂OH), 4.68 (broad s, 1H, —CH—O—CH—O—), 5.32 (m, 2H, —C=C$\underline{H}$—CH₂OH and

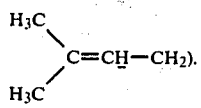

Further elution with 24% to 26% ethyl acetate gives (2S*, 3R*)-6E-(2''-hydroxyethylidene)-2-methyl-2-[4',8'-dimethyl-5'-(tetrahydropyran-2''-yloxy)-7'-nonenyl]-oxepan-3-ol (222 mg), 0.9 (d, 3H, J=6 Hz, —CH—C$\underline{H}_3$), 1.15 (s, 3H, CH$_3$),

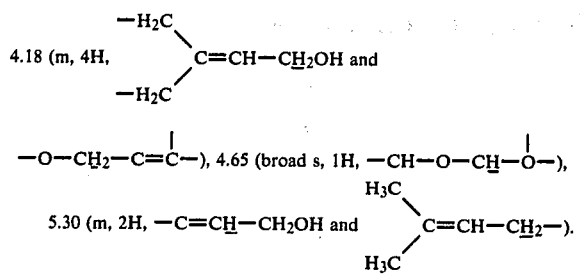

EXAMPLE M

(2S*, 3R*)-3-Acetoxy-6Z-(2''-acetoxyethylidene)-2-methyl-2-[4',8'-dimethyl-5'-(tetrahydropyran-2''-yloxy)-7'-nonenyl]-oxepane A solution of (2S*, 3R*)-6Z-(2''-hydroxyethylidene)-2-methyl-2-[4',8'-dimethyl-5'-(tetrahydropyran-2''-yloxy)-7'-nonenyl]-oxepan-3-ol (0.172 g, 0.00040 mole) in pyridine (2 ml) and acetic anhydride (0.2 ml) is stirred under nitrogen at 24° C. for 18 hours. The reaction mixture is then poured into water and stirred for 1.5 hours. The suspension is extracted with ether (5×50 ml) and the ether extracts washed with water, saturated copper sulfate solution, dried (MgSO$_4$) and evaporated in vacuo to give 170 mg of a yellowish oil. The oil is chromatographed on silica gel (2 g, Baker) in hexane. Elution with 10% ethyl acetate/hexane gives (2S*, 3R*)-3-acetoxy-6Z-(2''-acetoxyethylidene)-2-methyl-2-[4',8'-dimethyl-5'-(tetrahydropyran-2''-yloxy)-7'-nonenyl]-oxepane (166 mg, 82%): nmr (CDCl$_3$)δ

0.9 (d, 3H, J = 6 Hz, —C$\underline{H}$—CH$_3$), 1.20 (s, 3H, —$\overset{|}{\underset{|}{C}}$—C$\underline{H}_3$), 2.10 (s, 6H, —O—$\overset{O}{\overset{\|}{C}}$—C$\underline{H}_3$), 3.40 (m, 1H, —C$\underline{H}$—O—CH—O—), centered at 4.42 (m, 6H, —O—C$\underline{H}_2$—C=C, —C$\underline{H}$—OAc, —C=C—C$\underline{H}_2$—OAc and —O—C$\underline{H}$—O), 5.20 (m, 2H,
$\phantom{xxxx}\overset{|}{H}$

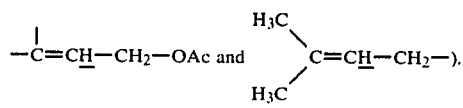

EXAMPLE N

(2S*, 3R*)-3-Acetoxy-6Z-(2''-acetoxyethylidene)-2-methyl-2-[4',8'-dimethyl-5'-hydroxy-7'-nonenyl]-oxepane A solution of (2S*, 3R*)-3-acetoxy-6Z-(2''-acetoxyethylidene)-2-methyl-2-[4',8'-dimethyl-5'-(tetrahydropyran-2''-yloxy)-7'-nonenyl]-oxepane (80 mg, 0.000157 moles), in acetic acid/water/tetrahydrofuran 20:10:1 (3 ml) is stirred under nitrogen at 40° C. for 4 hours. The reaction mixture is cooled and poured into ether (50 ml) and the ether washed with saturated sodium bicarbonate (50 ml). The ether phase is separated and the aqueous phase is extracted with ether (3×25 ml). The ether phases are combined and dried (MgSO$_4$). The solvents are removed under reduced pressure and the crude product (72 mg) is chromatographed on silica gel (1.1 g, Baker) in hexane. Elution with 8% ethyl acetate/hexane gives (2S*, 3R*)-3-acetoxy-6Z-(2''-acetoxyethylidene)-2-methyl-2-[4',8'-dimethyl-5-hydroxy-7'-nonenyl)-oxepane (61 mg, 90%): ir (neat) 3400 (OH), 1724 cm$^{-1}$ (OAc); nmr (CDCl$_3$)δ 0.90 (d, J=6 Hz, 3H, —CH—C$\underline{H}_3$), 1.22 (s, 3H, —C—C$\underline{H}_3$), 2.06 (s, 6H, 2-OCOC$\underline{H}_3$), 3.4 (m, 1H, CH$_2$—C$\underline{H}$—O$\underline{H}$—CH—), 4.3 (s, 2H, —O—C$\underline{H}_2$—$\overset{|}{C}$=CH—), 4.5 (d, 2H, —C=CH—C$\underline{H}_2$—OAc), 4.7 (m, 1H, —CH$_2$—C$\underline{H}$—OAc),

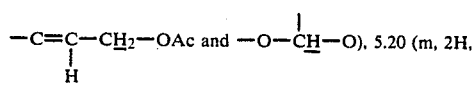

and —C=C$\underline{H}$—CH$_2$OAc).

EXAMPLE O

(2S*, 3R*)-3-Acetoxy-6Z-(2''-acetoxyethylidene)-2-methyl-2-[4',8'-dimethyl-5'-oxo-7'-nonenyl]-oxepane A pyridine-chromium trioxide solution [pyridine (345 mg, 0.00385 mole) and chromium trioxide (192 mg, 0.00192 mole)] is prepared in dry methylene chloride (27 ml) at 0° C. in a nitrogen atmosphere. The cooling bath is removed and celite (1.5 g) is added at 10° C. The solution is cooled to 0° C. and (2S*, 3R*)-3-acetoxy-6Z-(2''-acetoxyethylidene)-2-methyl-2-[4',8'-dimethyl-5'-hydroxy-7'-nonenyl]-oxepane (136 mg, 0.00032 mole) is added. After 1 hour, the mixture is filtered and the celite cake is washed with methylene chloride (10×10 ml). The organic phases are combined, washed with saturated sodium bicarbonate (2×25 ml), saturated sodium chloride and dried (MgSO$_4$). The solvent is removed at reduced pressure and the resulting crude product (140 mg) is chromatographed on (1.5 g, Baker) in hexane. Elution with 8% ethyl acetate/hexane gives (2S*, 3R*)-3-acetoxy-6Z-(2''-acetoxyethylidene)-2-methyl-2-[4',8'-dimethyl-5'-oxo-7'-nonenyl]-oxepane as a colorless oil (100 mg, 84%): ir (neat) 1740 (OAc), 1710 cm$^{-1}$ (CO), nmr (CDCl$_3$)δ 1.0 (d, 3H, J=6, Hz, CH—C$\underline{H}_3$), 1.16 (s, 3H, C$\underline{H}_3$), 2.05 (s, 6H, 2-OCOC$\underline{H}_3$),

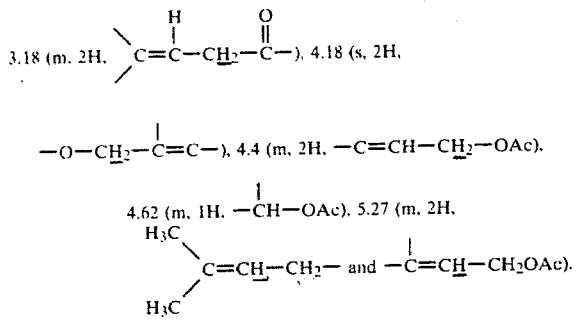

EXAMPLE P (2S*, 3R*)-3-Acetoxy-6E-(2″-acetoxyethylidene)-2-methyl-2-[4′,8′-dimethyl-5′-(tetrahydropyran-2″-yloxy)-7′-nonenyl]-oxepane A solution of (2S*, 3R*)-6E-(2″-hydroxyethylidene)-2-methyl-2-[4′,8′-dimethyl-5′-(tetrahydropyran-2″-yloxy)-7′-nonenyl]-oxepan-3-ol (252 mg, 0.000594 mole) in pyridine (3 ml) and acetic anhydride (0.3 ml) is stirred under nitrogen at 24° C. for 18 hours. The reaction mixture is then poured into water and stirred for 1.5 hours. The suspension is extracted with ether (5×50 ml) and the ether extracts are washed with water, saturated copper sulfate solution, dried (MgSO4) and evaporated in vacuo to give a yellowish oil (300 mg). The oil is chromatographed on silica gel (3 g, Baker) in hexane. Elution with 10% ethyl acetate/hexane gives (2S*, 3R*)-3-acetoxy-6E-(2″-acetoxyethylidene)-2-methyl-2-[4′,8′-dimethyl-5′-(tetrahydropyran-2″-yloxy)-7′-nonenyl]-oxepane (283 mg, 96%): nmr (CDCl3)δ 0.80 (d, J=6 Hz, 3H, CH—CH3), 0.90 (d, J=6 Hz, 3H, —CH—CH3),

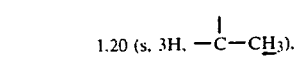

1.20 (s, 3H, —C—CH3).

2.01 (s, 6H, 2-OCOCH3),

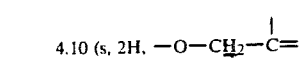

4.10 (s, 2H, —O—CH2—C=CH), 4.60 (m, 3H, —C=CH—CH2OAc and —CH—OAc),

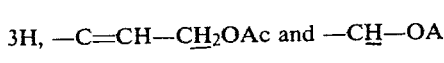

5.20 (m, 2H, —C=CH—CH2OAc and H3C\C=CH—CH2—/H3C).

EXAMPLE Q (2S*, 3R*)-3-Acetoxy-6E-(2″-acetoxyethylidene)-2-methyl-2-[4′,8′-dimethyl-5′-hydroxy-7′-nonenyl]-oxepane A solution of (2S*, 3R*)-3-acetoxy-6E-(2″-acetoxyethylidene)-2-methyl-2-[4′,8′-dimethyl-5′-(tetrahydropyran-2″-yloxy)-7′-nonenyl]-oxepane (280 mg, 0.00055 mole), in acetic acid/water/tetrahydrofuran 20:10:1 (5 ml) is stirred under nitrogen at 40° C. for 4 hours. The reaction mixture is cooled and poured into ether (50 ml) and the ether mixture is washed with saturated sodium bicarbonate (50 ml). The ether phase is separated and the aqueous phase is extracted with ether (4×50 ml). The ether phases are combined and dried (MgSO4). The solvents are removed under reduced pressure and the crude product (230 mg) is chromatographed on silica gel (2.3 g, Baker) in hexane. Elution with 8% ethyl acetate/hexane gives (2S*, 3R*)-3-acetoxy-6E-(2″-acetoxyethylidene)-2-methyl-2-[4′,8′-dimethyl-5′-hydroxy-7′-nonenyl]-oxepane (196 mg, 84%): nmr (CDCl3)δ 0.90 (d, J=6, 3H, CH—CH3), 1.19 (s, 3H, CH3), 2.05 (s, 6H, 2-O-COCH3), 3.40 (s, —CH2—CH—OH), 4.10 (s, 2H, —O—CH2—C=CH—), 4.60 (d, 2H, —C=CH—CH2—OAc—), 4.80 (m, 1H, —CH—OAc), 5.30 (m, 2H,

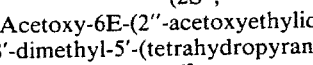

H3C\C=CH—CH2—and —C=CHCH2OAc).
/H3C

EXAMPLE R (2S*, 3R*)-3-Acetoxy-6E-(2″-acetoxyethylidene)-2-methyl-2-[4′,8′-dimethyl-5′-oxo-7′-nonenyl]-oxepane A solution of pyridine (440 mg, 0.00558 mole) and chromium trioxide (279 mg, 0.00279 mole) in methylene chloride (25 ml) in a nitrogen atmosphere is stirred for 45 minutes at 0° C. Celite (2 g) is added followed by (2S*, 3R*)-3-acetoxy-6E-(2″-acetoxyethylidene)-2-methyl-2-[4′,8′-dimethyl-5′-hydroxy-7′-nonenyl]-oxepane (197 mg, 0.000465 mole) in methylene chloride (25 ml). The mixture is stirred for 90 minutes at 23° C. The mixture is then filtered and the celite cake is washed with methylene chloride (10×10 ml). The filtrate and the washings are combined and the methylene chloride extracts are washed with sodium bicarbonate, water and saturated sodium chloride, dried (MgSO4), and evaporated in vacuo. The crude product (201 mg) is chromatographed on silica gel (3 g, Baker) in hexane. Elution with 8% ethyl acetate/hexane gives (2S*, 3R*)-3-acetoxy-6E-(2″-acetoxyethylidene)-2-methyl-2-[4′,8′-dimethyl-5′-oxo-7′-nonenyl]-oxepane as a colorless oil (173 mg, 88%): ir (neat) 1710 (CO), 1740 (OAc) cm−1, nmr (CDCl3)δ 1.0 (d, 3H, J=6 Hz, —CHCH3),

1.18 (s, 3H, —C—CH3), 1.62–1.78 (two singlets, 6H,

—C=C(CH3)(CH3)), 2.02 (s, 6H, 2-O—C(=O)—CH3), 3.10 (s, 2H,

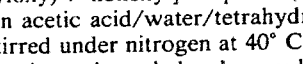

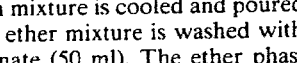

4.58 (d, 2H, J = 6 Hz, —C=CH—CH2OAc), 4.80 (broad m,

-continued

1H, —CH—OAc), 5.15 (m, 2H, —H₂C—CH—C=C(CH₃)(CH₃) and

—C=CH—CH₂—OAc).

EXAMPLE S

(2S*, 3R*)-6E-(2″-Hydroxyethylidene)-2-methyl-2-[4′,8′-dimethyl-5′-oxo-7′-nonenyl]-oxepan-3-ol A solution of (2S*, 3R*)-3-acetoxy-6E-(2″-acetoxyethylidene)-2-methyl-2-[4′,8′-dimethyl-5′-oxo-7′-nonenyl]-oxepane (173 mg, 0.000410 mole), 40% solution of tetrabutylammonium hydroxide in methanol (1 ml), water (4 ml) and tetrahydrofuran (4 ml) at 25° C. in a nitrogen atmosphere is stirred for 24 hours. The solution is then diluted with saturated sodium chloride (50 ml) and the aqueous layer is extracted with ethyl acetate (5×50 ml). The combined organic layers are dried (MgSO₄) and evaporated in vacuo. The crude product (170 mg) is chromatographed on silica gel (3.5 g, Baker) in chloroform. Elution with chloroform gives (2S*, 3R*)-6E-(2″-hydroxyethylidene)-2-methyl-2-[4′,8′-dimethyl-5′-oxo-7′-nonenyl]-oxepan-3-ol as a colorless oil (110 mg, 80%): ir (neat) 3448 (OH) 1709 (CO) cm⁻¹, 5.41 (m, 2H, —C=CH—CH₂OH and —C=CH—CH₂OH and —C=CHCH₂—C(=O)—), 4.18 (d, 2H, J = 6 Hz, —C=CH—CH₂—OH), 4.10 (s, 2H, —O—CH₂—C=C), 3.40 (m, 1H, —CH₂—CH(OH)—C—), 3.17 (d, 2H, (CH₃)₂C=CH—CH₂CO—C—), 1.64 (d, 6H, —HC=C—(CH₃)₂), 1.18 (s, 3H, —C(CH₃)—CH₃), 1.05 (d, J=6, Hz, 3H, —CH—CH₃); Mass spectrum m/e, 320 (m-18), 302 (m-2H₂O), 251, 233, 141, 125, 113, 97, 95, 81, 69.

EXAMPLE T

(2S*, 3R*)-6Z-(2″-Hydroxyethylidene)-2-methyl-2-[4′,8′-dimethyl-5′-oxo-7′-nonenyl]-oxepan-3-ol A solution of (2S*, 3R*)-3-acetoxy-6Z-(2″-acetoxyethylidene)-2-methyl-2-[4′,8′-dimethyl-5′-oxo-7′-nonenyl]-oxepane (100 mg, 0.000236 mole), 40% solution of tetrabutylammonium hydroxide in methanol (1 ml), water (4 ml) and tetrahydrofuran (4 ml) at 25° C. in a nitrogen atmosphere is stirred for 24 hours. The solution is diluted with saturated sodium chloride (50 ml) and the aqueous layer is extracted with ethyl acetate (5×50 ml). The combined organic layers are dried (MgSO₄) and evaporated in vacuo. The crude product (210 mg) is chromatographed on silica gel (1.5 g, Baker) in chloroform. Elution with chloroform gives (2S*, 3R*)-6Z-(2″-hydroxyethylidene)-2-methyl-2-[4′,8′-dimethyl-5′-oxo-7′-nonenyl]-oxepan-3-ol as a colorless oil (65 mg, 81%): ir (neat) 3448 (OH), 1709 (CO) cm⁻¹, nmr (CDCl₃)δ

5.41 (m, 2H, —C=CH—CH₂OH and (H₃C)(H₃C)C=CH—CH₂C(=O)—), 4.22 (s, 2H, —O—CH₂—C=C—), 4.05 (d, 2H, J = 4 Hz, C—CH—CH₂OH), 3.50 broad t, 1H, —CH(OH)—OH), 3.17 (d, 2H, C=CH—CH₂—C(=O)—C), 1.7.

[(d, 6H, —C=C—(CH₃)₂)], 1.16 (s, 3H, —C(CH₃)—CH₃), 1.07 (d, 3H, J=6 Hz, —CH—CH₃); Mass spectrum m/e, 320 (m-18), 302 (M⊕-2H₂O), 251, 233, 141, 125, 113, 97, 95, 81, 69.

What is claimed is:

1. The process for the preparation of a compound of the formula

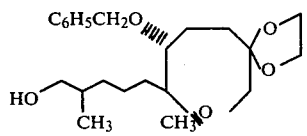

which comprises reacting a compound of the formula

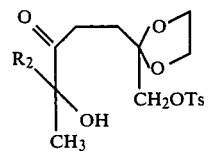

with dimethyl sulfoxide in an alkyl anhydride to form a compound of the formula

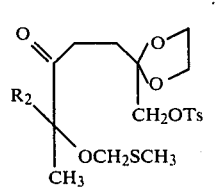

reacting the product formed with sodium borohydride to form a mixture of the erythro and threo alcohols of the formula

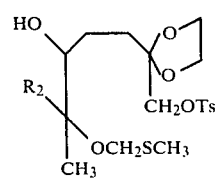

chromatographing the mixture over an adsorbent material to separate the isomers, reacting the erythro isomer with a mixture of mercuric chloride and calcium carbonate to form an erythro diol of the formula

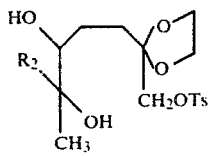

reacting the product with a benzyl halide to form an erythro benzyl ether of the formula

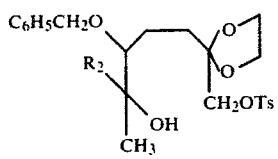

and reacting the product with a base in dimethyl sulfoxide wherein $R_2$ is $-(CH_2)_3CH(CH_3)CH_2OSi(C_6H_5)_2t-C_4H_9$; and wherein $R_2$ is $-(CH_2)_3CH(CH_3)CH_2OCH_2OCH_2CH_2OCH_3$ reacting the product with a base in dimethyl sulfoxide followed by reaction with zinc chloride; and wherein $R_2$ is $-(CH_2)_3C(CH_3)=CH_2$ reacting the product wth a base in dimethyl sulfoxide followed by reaction with borane methylsulfide.

2. The process of claim 1 wherein $R_2$ is $-(CH_2)_3CH(CH_3)CH_2OSi(C_6H_5)_2t-C_4H_9$.

3. The process of claim 1 wherein $R_2$ is $-(CH_2)_3CH(CH_3)CH_2OCH_2OCH_2CH_2OCH_3$.

4. The process of claim 1 wherein $R_2$ is $-(CH_2)_3C(CH_3)=CH_2$.

5. The process of claim 1 wherein the adsorbent material is silica gel.

6. The process of claim 1 wherein the benzyl halide is benzyl bromide.

7. The process of claim 1 wherein the alkyl anhydride is acetic anhydride.

8. The process of claim 1 wherein the base is sodium hydride.

9. The process for the preparation of a compound of the formula

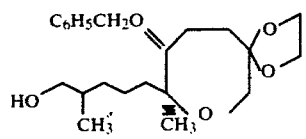

which comprises reacting a compound of the formula

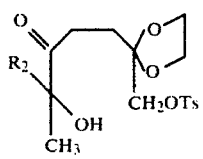

with dimethyl sulfoxide in an alkyl anhydride to form a compound of the formula

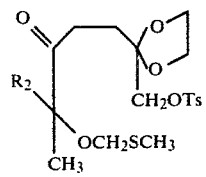

reacting the product formed with sodium borohydride to form an epimeric mixture of the erythro and threo alcohols of the formula

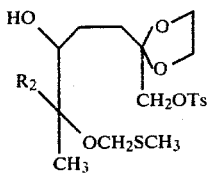

reacting said mixture with a mixture of mercuric chloride and calcium carbonate to form a product of the formula

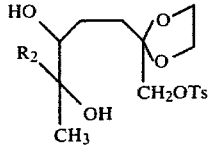

reacting said product with a benzyl halide to form a mixture of compounds of the formula

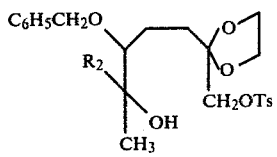

chromatographing the mixture over an adsorbent material to separate the isomers and reacting the erythro isomer with a base in dimethyl sulfoxide, wherein $R_2$ is $-(CH_2)_3CH(CH_3)CH_2OSi(C_6H_5)_2t-C_4H_9$; and wherein $R_2$ is $-(CH_2)_3C(CH_3)-CH_2O-CH_2OCH_2CH_2OCH_3$ reacting the said product with a base in dimethyl sulfoxide followed by reaction with zinc chloride; and wherein $R_2$ is $-(CH_2)_3C(CH_3)=CH_2$ reacting the product with a base in dimethyl sulfoxide followed by reaction with borane methylsulfide.

10. The process of claim 9 wherein $R_2$ is $-(CH_2)_3CH(CH_3)CH_2OSi(C_6H_5)_2t-C_4H_9$.

11. The process of claim 9 wherein $R_2$ is $-(CH_2)_3CH(CH_3)CH_2OCH_2OCH_2CH_2OCH_3$.

12. The process of claim 9 wherein $R_2$ is $-(CH_2)_3C(CH_3)=CH_2$.

13. The process of claim 9 wherein the benzyl halide is benzyl bromide.

14. The process of claim 9 wherein the alkyl anhydride is acetic anhydride.

15. The process of claim 9 wherein the adsorbent material is silica gel.

16. The process of claim 9 wherein the base is sodium hydride.

* * * * *